(12) United States Patent  
Floros et al.

(10) Patent No.: US 11,384,260 B1  
(45) Date of Patent: Jul. 12, 2022

(54) ADHESIVE DEVICES AND USES THEREOF

(71) Applicant: Cohesys Inc., Toronto (CA)

(72) Inventors: Michael C. Floros, Toronto (CA); Latchmi Raghunanan, Toronto (CA); Alexander J. Lausch, Toronto (CA); Janaina Freitas Bortolatto, Toronto (CA); Bryan Donovan Quan, Toronto (CA)

(73) Assignee: Cohesys Inc., Toronto (CA)

( * ) Notice: Subject to any disclaimer, the term of this patent is extended or adjusted under 35 U.S.C. 154(b) by 0 days.

(21) Appl. No.: 17/340,313

(22) Filed: Jun. 7, 2021

Related U.S. Application Data

(60) Provisional application No. 63/194,297, filed on May 28, 2021.

(51) Int. Cl.

| | |
|---|---|
| *A61B 17/58* | (2006.01) |
| *A61B 17/60* | (2006.01) |
| *A61F 2/00* | (2006.01) |
| *C09J 7/25* | (2018.01) |
| *C09J 7/35* | (2018.01) |
| *C09J 11/04* | (2006.01) |
| *A61L 24/02* | (2006.01) |
| *A61L 24/04* | (2006.01) |
| *C08L 53/00* | (2006.01) |
| *C08L 67/04* | (2006.01) |

(52) U.S. Cl.  
CPC ............... *C09J 7/255* (2018.01); *A61L 24/02* (2013.01); *A61L 24/043* (2013.01); *C08L 53/00* (2013.01); *C08L 67/04* (2013.01); *C09J 7/35* (2018.01); *C09J 11/04* (2013.01); *C09J 2301/304* (2020.08); *C09J 2301/408* (2020.08); *C09J 2400/163* (2013.01); *C09J 2467/00* (2013.01); *C09J 2467/006* (2013.01)

(58) Field of Classification Search  
CPC ............................. A61L 24/02; A61L 24/043  
See application file for complete search history.

(56) References Cited

U.S. PATENT DOCUMENTS

| | | | |
|---|---|---|---|
| 3,480,492 | A | 11/1969 | Hauser |
| 5,266,608 | A | 11/1993 | Katz et al. |
| 5,749,895 | A | 5/1998 | Sawyer et al. |
| 6,066,176 | A | 5/2000 | Oshida |
| 6,486,232 | B1 | 11/2002 | Wise et al. |
| 6,666,870 | B2 | 12/2003 | Dixon et al. |
| 7,066,962 | B2 | 6/2006 | Swords |
| 7,335,210 | B2 | 2/2008 | Smit |
| 7,842,146 | B2 | 11/2010 | Siavoshani et al. |

(Continued)

FOREIGN PATENT DOCUMENTS

| | | |
|---|---|---|
| CA | 2268478 A1 | 2/1999 |
| CA | 2777668 C | 2/2019 |

(Continued)

OTHER PUBLICATIONS

Office Action for U.S. Appl. No. 17/338,951, dated Oct. 14, 2021 (15 pages).

(Continued)

*Primary Examiner* — Sameh R Boles  
(74) *Attorney, Agent, or Firm* — Clark & Elbing LLP

(57) ABSTRACT

The invention features adhesive devices for holding objects (e.g., bone fragments) fixed with respect to each other.

30 Claims, 2 Drawing Sheets

(56) References Cited

U.S. PATENT DOCUMENTS

| | | | |
|---|---|---|---|
| 7,967,820 | B2 | 6/2011 | Bonutti et al. |
| 8,221,475 | B2 | 7/2012 | Aeschlimann et al. |
| 8,398,720 | B2 | 3/2013 | Swords |
| 8,403,968 | B2 | 3/2013 | Rabiner et al. |
| 8,431,226 | B2 | 4/2013 | Huerta et al. |
| 8,673,354 | B2 | 3/2014 | Bianco-Peled et al. |
| 8,754,285 | B2 | 6/2014 | Lee et al. |
| 8,815,973 | B2 | 8/2014 | Lin et al. |
| 8,893,790 | B2 | 11/2014 | Reyes et al. |
| 8,916,652 | B2 | 12/2014 | Dalsin et al. |
| 8,962,772 | B2 | 2/2015 | Ding et al. |
| 8,968,716 | B2 | 3/2015 | Park et al. |
| 9,163,169 | B2 | 10/2015 | Balogh et al. |
| 9,228,112 | B2 | 1/2016 | Gorodisher et al. |
| 9,260,641 | B2 | 2/2016 | Fant |
| 9,283,298 | B2 | 3/2016 | Nagatomi et al. |
| 9,296,843 | B2 | 3/2016 | Messersmith et al. |
| 9,303,048 | B2 | 4/2016 | Hirokami |
| 9,332,991 | B2 | 5/2016 | Pereira et al. |
| 9,370,385 | B2 | 6/2016 | Weinzweig |
| 9,447,407 | B2 | 9/2016 | Zink et al. |
| 9,466,544 | B2 | 10/2016 | Uehling |
| 9,572,910 | B2 | 2/2017 | Messersmith et al. |
| 9,597,133 | B2 | 3/2017 | McCarthy et al. |
| 9,687,582 | B2 | 6/2017 | Messersmith et al. |
| 9,750,842 | B2 | 9/2017 | Kourtis et al. |
| 10,045,801 | B2 | 8/2018 | Whyne et al. |
| 10,646,264 | B2 | 5/2020 | Whyne et al. |
| 2004/0037906 | A1 | 2/2004 | Li et al. |
| 2005/0201974 | A1 | 9/2005 | Schestopol et al. |
| 2006/0045864 | A1 | 3/2006 | Martensson et al. |
| 2007/0173949 | A1 | 7/2007 | Sharps et al. |
| 2008/0169059 | A1 | 7/2008 | Messersmith et al. |
| 2008/0247984 | A1 | 10/2008 | Messersmith et al. |
| 2009/0044895 | A1 | 2/2009 | Fortune et al. |
| 2009/0076241 | A1 | 3/2009 | Lee |
| 2009/0254006 | A1 | 10/2009 | Babaev |
| 2010/0137903 | A1 | 6/2010 | Lee et al. |
| 2010/0330025 | A1 | 12/2010 | Messersmith et al. |
| 2011/0086095 | A1 | 4/2011 | Jacob et al. |
| 2011/0105712 | A1 | 5/2011 | Jiang et al. |
| 2012/0093895 | A1 | 4/2012 | Song et al. |
| 2013/0023879 | A1 | 1/2013 | Kerr et al. |
| 2013/0052712 | A1 | 2/2013 | Cha et al. |
| 2013/0053898 | A1 | 2/2013 | Voisard et al. |
| 2013/0183630 | A1 | 7/2013 | Krikorian et al. |
| 2014/0058184 | A1 | 2/2014 | Crawford |
| 2014/0221485 | A1 | 8/2014 | Gunther et al. |
| 2014/0277399 | A1 | 9/2014 | Pacetti et al. |
| 2014/0311673 | A1* | 10/2014 | Zhao et al. |
| 2014/0315955 | A1 | 10/2014 | Chung et al. |
| 2015/0114261 | A1 | 4/2015 | Thevasahayam |
| 2015/0182670 | A1 | 7/2015 | Rizk et al. |
| 2015/0322243 | A1 | 11/2015 | Jaerger et al. |
| 2015/0361310 | A1 | 12/2015 | Combs et al. |
| 2016/0032047 | A1 | 2/2016 | Murphy et al. |
| 2016/0160097 | A1 | 6/2016 | Waite et al. |
| 2016/0263136 | A1 | 9/2016 | Cha et al. |
| 2017/0056548 | A1 | 3/2017 | Lee et al. |
| 2017/0065495 | A1 | 3/2017 | Eckert et al. |
| 2017/0210852 | A1 | 7/2017 | Becker et al. |
| 2019/0022273 | A1* | 1/2019 | Hess .................. A61B 17/70 |
| 2019/0038328 | A1 | 2/2019 | Whyne et al. |
| 2019/0262276 | A1 | 8/2019 | Zilberman et al. |

FOREIGN PATENT DOCUMENTS

| | | |
|---|---|---|
| CN | 107868645 A | 4/2018 |
| DE | 10358779 A1 | 7/2005 |
| DE | 60118256 T2 | 12/2006 |
| EP | 1488753 A1 | 12/2004 |
| EP | 2614810 A2 | 7/2013 |
| WO | WO-2005/056680 A1 | 6/2005 |
| WO | WO-2008/080239 A1 | 7/2008 |
| WO | WO-2009/029908 A1 | 3/2009 |
| WO | WO-2009/137190 A2 | 11/2009 |
| WO | WO-2011/048077 A2 | 4/2011 |
| WO | WO-2011/115420 A2 | 9/2011 |
| WO | WO-2012/004570 A2 | 1/2012 |
| WO | WO-2014/019083 A1 | 2/2014 |
| WO | WO-2014/118266 A1 | 8/2014 |
| WO | WO-2014/138190 A1 | 9/2014 |
| WO | WO-2014/195169 A1 | 12/2014 |
| WO | WO-2016/010484 A1 | 1/2016 |
| WO | WO-2016/049029 A1 | 3/2016 |
| WO | WO-2017/004174 A1 | 1/2017 |
| WO | WO-2017/044896 A1 | 3/2017 |
| WO | WO-2017/095782 A1 | 6/2017 |
| WO | WO-2021/119853 A1 | 6/2021 |
| WO | WO-2021/119854 A1 | 6/2021 |
| WO | WO-2021/119855 A1 | 6/2021 |

OTHER PUBLICATIONS

Response to Non-Final Office Action for U.S. Appl. No. 17/338,951, dated Jan. 10, 2022 (8 pages).

* cited by examiner

ADHESIVE DEVICES AND USES THEREOF

BACKGROUND

Surgical adhesives designed to interface with tissues, especially for internal use, must be biocompatible, easy to apply, and able to adhere to biological tissues under wet, dry, clean and/or biofouled conditions. These requirements, however, greatly limit the application of surgical adhesives in biomedical applications, with current commercially available surgical adhesives presenting one or more of undesirable strength, toxicity, difficult workflow, and/or requiring clean, dry surfaces for optimal performance.

Severe traumatic craniomaxillofacial (CMF) fracture commonly occurs due to high energy trauma such as motor vehicle accidents, sports injuries, war injuries, and physical assault. Many of these fractures require surgical stabilization and/or reconstructed. Current adhesives that may be used to stabilize CMF and other fractures suffer from one or more of the following deficiencies: high water solubility, weak bond strength, a curing time that is either too slow or too fast, irreversible rigid curing that does not allow proper reduction, and a lack of biocompatibility. Therefore, there exists a need for new bioadhesives.

SUMMARY OF THE INVENTION

The invention features adhesive devices for holding objects (e.g., bone fragments) fixed in position with respect to each other.

In a first aspect, the invention features a method for stabilizing bone fragments in a body, the method comprising the steps of:

(i) forming a first anchor on a first bone fragment by (a) heating an adhesive composition to form a softened adhesive composition and contacting the softened adhesive composition to the first bone fragment, and (b) permitting the softened adhesive composition to cool to form the first anchor affixed to the first bone fragment;

(ii) forming a second anchor on a second bone fragment by (a) heating an adhesive composition to form a softened adhesive composition and contacting the softened adhesive composition to the second bone fragment, and (b) permitting the softened adhesive composition to cool to form the second anchor affixed to the second bone fragment;

wherein the adhesive composition has a tackifying temperature of at least 40° C. (e.g., at least 42° C., at least 45° C., at least 50° C., at least 55° C., or between from 40° C. to 55° C.), and wherein the first anchor and the second anchor are connected to a support structure for stabilizing the bone fragments.

In some embodiments, the support structure is a flexible support comprising a biodegradable and biocompatible polymer linking the first anchor to the second anchor. In some embodiments, the support structure, the first anchor, and the second anchor are formed from a tape comprising (x) a non-adhesive top layer that is the support structure, and (y) a bottom layer that is adhesive when softened to form the first anchor and the second anchor.

In some embodiments, the adhesive composition is not water soluble (e.g., has a water solubility at 25° C. of less than 30 mg/L, 25 mg/L, 20 mg/L, or 15 mg/L). In other embodiments, the adhesive composition is water soluble (e.g., has a solubility in water at 25° C. of greater than 30 mg/L or 50 mg/L).

In some embodiments, the adhesive composition comprises an inorganic particulate additive heat transfer agent. In some embodiments, the heat transfer agent (e.g., sodium chloride, iron(III) phosphate dihydrate, iron(III) citrate monohydrate, hydroxyapatite, tetracalcium phosphate, and sodium carbonate, or a combination thereof (e.g., hydroxyapatite)) is present in an amount that permits the softened adhesive composition to cool and harden in 120 seconds or less (e.g., 10 seconds or less). In some embodiments, the heat transfer agent is present in an amount that permits the adhesive composition to soften within 120 seconds or less of applying energy (e.g., within 10 seconds or less). In particular embodiments, the heat transfer agent is present in an amount that permits the adhesive composition to soften within 10 seconds or less of applying energy to the non-adhesive top layer. In some embodiments, the adhesive composition comprises about 0.5-60% (w/w) heat transfer agent (e.g., 7.5±2.5%, 10±5%, 15±5%, 20±5%, 25±10%, 37.5±5%, 50±10%, or 35-60% (w/w)).

In some embodiments, the adhesive composition comprises a polymer having the structure of formula (I):

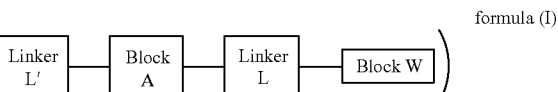
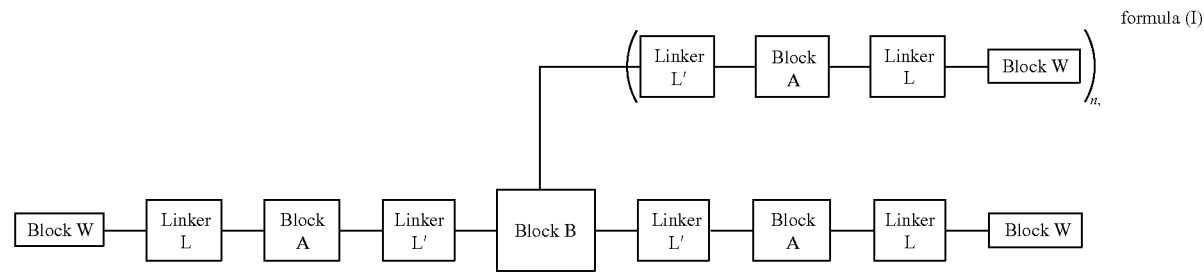

wherein n is an integer from 0 to 4 (e.g., n=1, 2, 3, or 4);

Block B comprises an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A comprises an optionally substituted $C_1$-$C_6$ alkylene, wherein Block A is derived from a diisocyanate crosslinker;

Block W comprises an optionally substituted $C_0$-$C_3$ alkyl-benzene-diol or optionally substituted $C_0$-$C_3$ alkyl-benzene-triol;

Linker L' comprises a carbamate; and

Linker L comprises a urea.

In some embodiments, Block B comprises an oligomer derived from a polyester, polalkylene glycol, polysilicone, or polycarbonate. In particular embodiments, the Block B oligomer has a MW≤4,000 g/mol (e.g., 1±0.5 KDa, 2±0.5 KDa, or 3±1 KDa).

In some embodiments, Block B has the structure of formula (II):

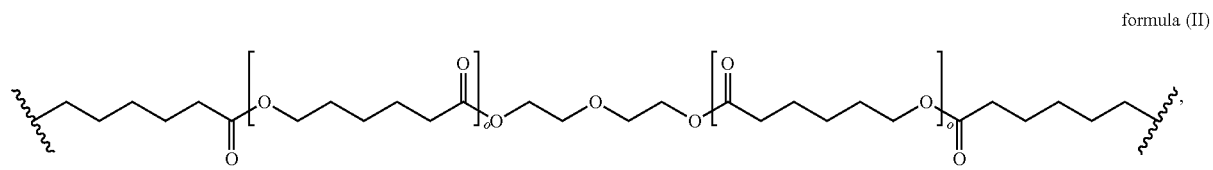

formula (II)

wherein each o is, independently, an integer from 0 to 20 (e.g., n=0-4, 2-6, 4-10, 5-15, or 10-20).

In some embodiments, Block B has the structure of formula (III):

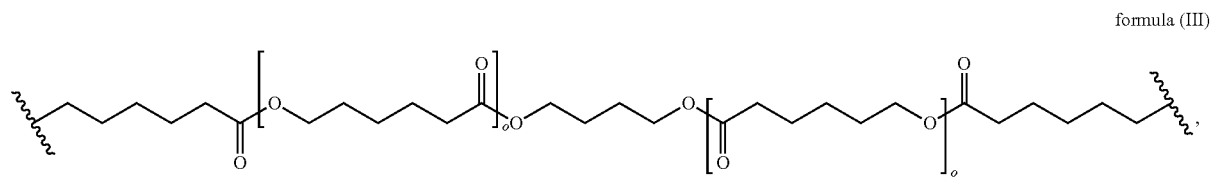

formula (III)

wherein each o is, independently, an integer from 0 to 20 (e.g., n=0-4, 2-6, 4-10, 5-15, or 10-20).

In some embodiments, Block B has the structure of formula (IV):

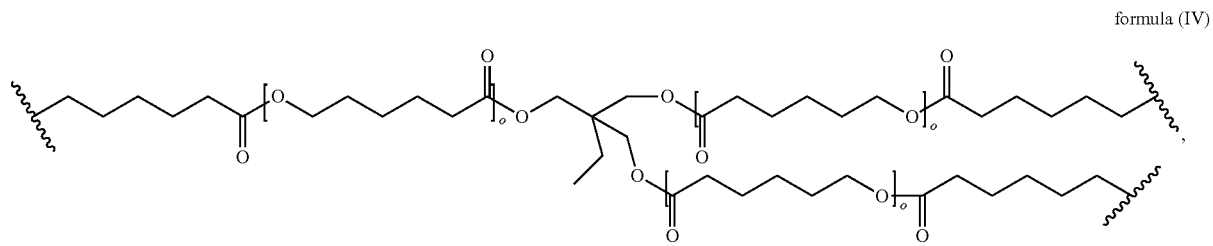

formula (IV)

wherein each o is, independently, an integer from 0 to 20 (e.g., n=0-4, 2-6, 4-10, 5-15, or 10-20).

In some embodiments, Block B has the structure of formula (V)

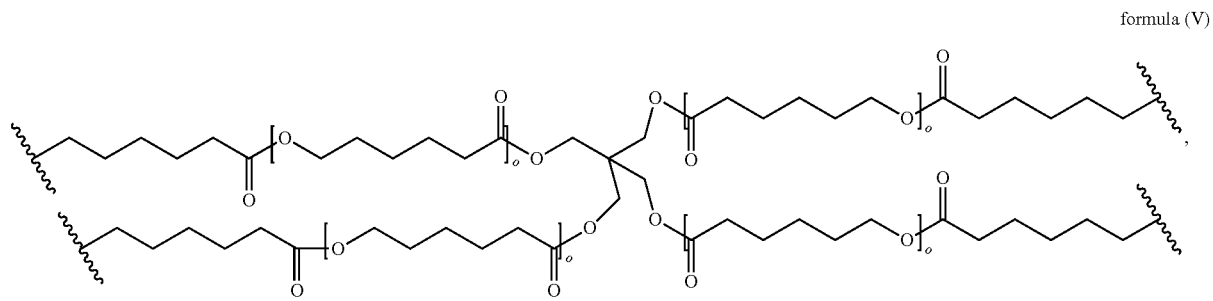

formula (V)

wherein each o is, independently, an integer from 0 to 20 (e.g., n=0-4, 2-6, 4-10, 5-15, or 10-20).

In some embodiments, Block B has the structure of formula (VI):

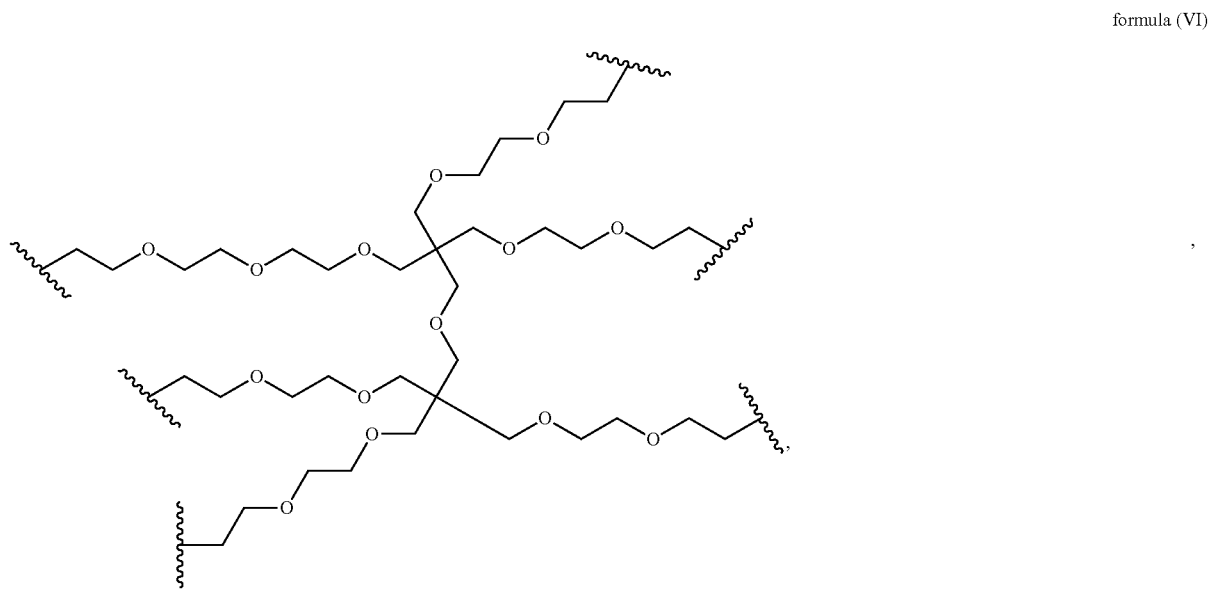 [SMILES: *CCOCCOCCOCC(COCCOCC*)(COCCOCC*)COCC(CCOCCOCC*)(COCCOCC*)COCCOCC*]

formula (VI)

wherein each o is, independently, an integer from 0 to 20 (e.g., n=0-4, 2-6, 4-10, 5-15, or 10-20).

In some embodiments, Block A has the structure of formula (VII):

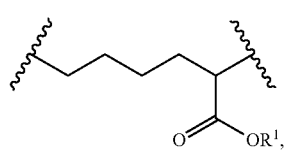

formula (VII)

wherein $R^1$ is $C_1$-$C_3$ alkyl.

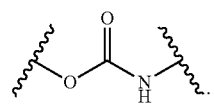

In some embodiments, Linker L' has the structure:

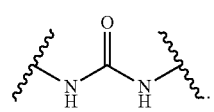

In some embodiments, Linker L has the structure:

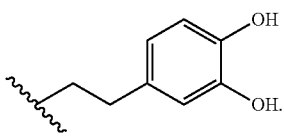 [SMILES: *CCc1ccc(O)c(O)c1]

In some embodiments, Block W has the structure:

In some embodiments, the adhesive composition comprises from 30-70% (w/w) of a filler.

In some embodiments, the filler comprises polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof, or a blend thereof. In some embodiments, the filler comprises polycaprolactone (PCL), polydioxanone (PDX), poly (lactic-co-glycolic acid) (PLGA), or poly-3-hydroxybutyrate (P3HB), or a copolymer thereof, or a blend thereof.

In some embodiments, step (i) and step (ii) are repeated to stabilize a plurality of bone fragments in a subject. In some embodiments, from 2 to 5, 6 to 10, 11 to 15, 16 to 20, 21 to 25, 26 to 30, 31 to 35, 36 to 40, 41 to 45, 46 to 50 or more bone fragments are stabilized in a subject.

In a second aspect, the invention features a device for stabilizing bone fragments in a body, the device comprising:
(i) a first anchor on a first bone fragment, the first anchor comprising an adhesive composition that softens with heating and forms the first anchor affixed to the first bone fragment upon cooling;
(ii) a second anchor on a second bone fragment, the second anchor comprising an adhesive composition that softens with heating and forms the second anchor affixed to the second bone fragment upon cooling;

(iii) a support structure connecting the first anchor to the second anchor for stabilizing the bone fragments;

wherein the adhesive composition has a tackifying temperature of at least 40° C. (e.g., at least 42° C., at least 45° C., at least 50° C., at least 55° C., or between from 40° C. to 55° C.).

In some embodiments of the second aspect, the support structure is a flexible support comprising a biodegradable and biocompatible polymer linking the first anchor to the second anchor. In some embodiments, the support structure, the first anchor, and the second anchor are formed from a tape comprising (x) a non-adhesive top layer that is the support structure, and (y) a bottom layer that is adhesive when softened to form the first anchor and the second anchor.

In some embodiments of the second aspect, the adhesive composition is not water soluble.

In some embodiments of the second aspect, the adhesive composition comprises a heat transfer agent. In some embodiments, the heat transfer agent (e.g., sodium chloride, iron(III) phosphate dihydrate, iron(III) citrate monohydrate, hydroxyapatite, tetracalcium phosphate, and sodium carbonate, or a combination thereof (e.g., hydroxyapatite)) is present in an amount that permits the softened adhesive composition to cool and harden in 120 seconds or less (e.g., within 10 seconds or less). In some embodiments, the heat transfer agent is present in an amount that permits the adhesive composition to soften within 120 seconds or less of applying energy (e.g., within 10 seconds or less). In some embodiments, the heat transfer agent comprises about 0.5-60% (w/w) of the adhesive composition (e.g., 7.5±2.5%, 10±5%, 15±5%, 20±5%, 25±10%, 37.5±5%, 50±10%, or 35-60% (w/w)).

In some embodiments of the second aspect, the adhesive composition comprises a polymer having the structure of formula (I):

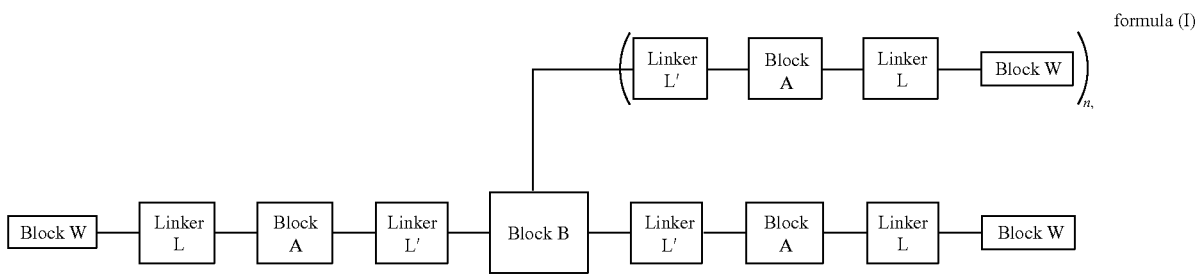

formula (I)

wherein n is an integer from 0 to 4 (e.g., n=1, 2, 3, or 4);

Block B comprises an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A comprises an optionally substituted $C_1$-$C_6$ alkylene, wherein Block A is derived from a diisocyanate crosslinker;

Block W comprises an optionally substituted $C_0$-$C_3$ alkyl-benzene-diol or optionally substituted $C_0$-$C_3$ alkyl-benzene-triol;

Linker L' comprises a carbamate; and

Linker L comprises a urea.

In some embodiments, Block B comprises an oligomer derived from a polyester, polalkylene glycol, polysilicone, or polycarbonate. In particular embodiments, the Block B oligomer has a MW≤4,000 g/mol (e.g., 1±0.5 KDa, 2±0.5 KDa, or 3±1 KDa).

In some embodiments of the second aspect of the invention, Block B has the structure of formula (II):

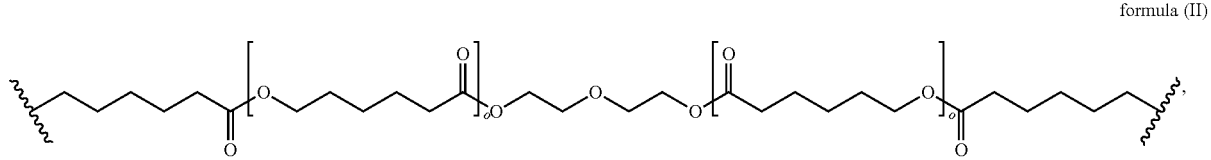

formula (II)

wherein each o is, independently, an integer from 0 to 20 (e.g., n=0-4, 2-6, 4-10, 5-15, or 10-20).

In some embodiments of the second aspect of the invention, Block B has the structure of formula

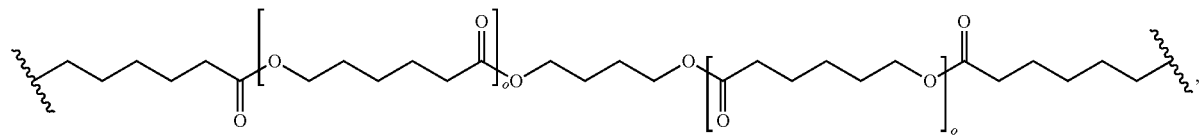

formula (III)

wherein each o is, independently, an integer from 0 to 20 (e.g., n=0-4, 2-6, 4-10, 5-15, or 10-20).

In some embodiments of the second aspect of the invention, Block B has the structure of formula (IV):

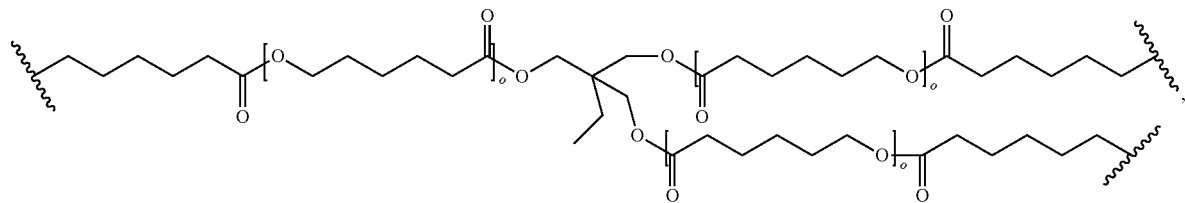

formula (IV)

wherein each o is, independently, an integer from 0 to 20 (e.g., n=0-4, 2-6, 4-10, 5-15, or 10-20).

In some embodiments of the second aspect of the invention, Block B has the structure of formula (V)

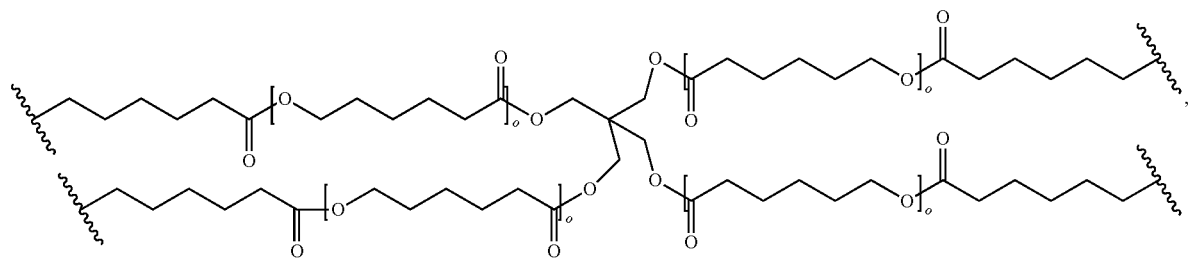

formula (V)

wherein each o is, independently, an integer from 0 to 20 (e.g., n=0-4, 2-6, 4-10, 5-15, or 10-20).

In some embodiments of the second aspect of the invention, Block B has the structure of formula (VI):

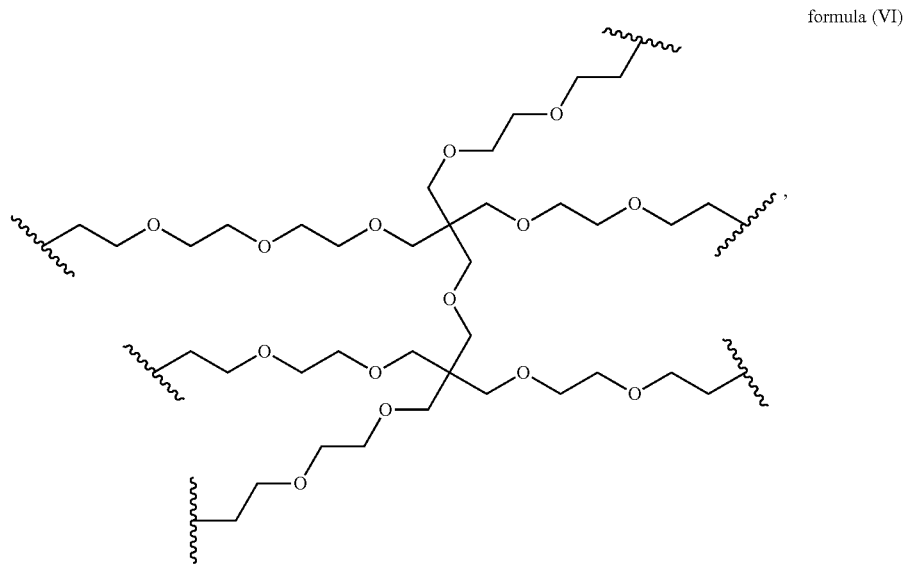 [SMILES: *CCOCCOCCOCC(COCCOCC*)(COCCOCC*)COCC(COCCOCC*)(COCCOCC*)COCCOCC*]

formula (VI)

wherein each o is, independently, an integer from 0 to 20 (e.g., n=0-4, 2-6, 4-10, 5-15, or 10-20).

In some embodiments of the second aspect of the invention, Block A has the structure of formula (VII):

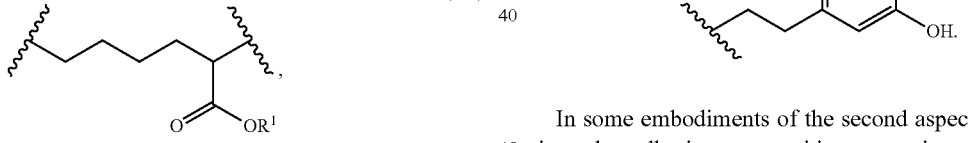

formula (VII)

wherein $R^1$ is $C_1$-$C_3$ alkyl.

In some embodiments of the second aspect of the invention, Linker L' has the structure:

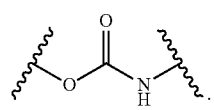 [SMILES: *NC(=O)O*]

In some embodiments of the second aspect of the invention, Linker L has the structure:

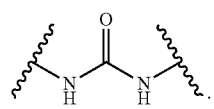 [SMILES: *NC(=O)N*]

In some embodiments of the second aspect, Block W has the structure:

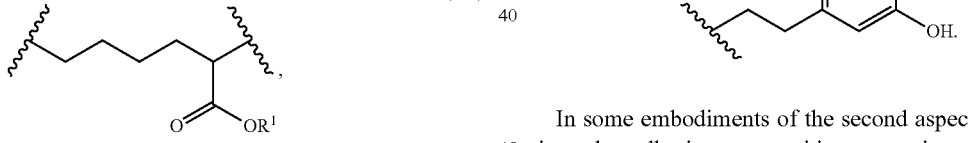

In some embodiments of the second aspect of the invention, the adhesive composition comprises from 30-70% (w/w) of a filler (e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof, or a blend thereof). In some embodiments, the filler comprises polycaprolactone (PCL), polydioxanone (PDX), poly(lactic-co-glycolic acid) (PLGA), or poly-3-hydroxybutyrate (P3HB), or a copolymer thereof, or a blend thereof.

In some embodiments of the second aspect of the invention, the device comprises a plurality of bone anchors and a plurality of support structures to stabilize a plurality of bone fragments in a subject.

In a third aspect, the invention features an adhesive composition comprising:
(i) from 0-70% (w/w) of a filler; and
(ii) from 30-100% (w/w) of a polymer (e.g., 30-35% (w/w)) having the structure of formula (I):

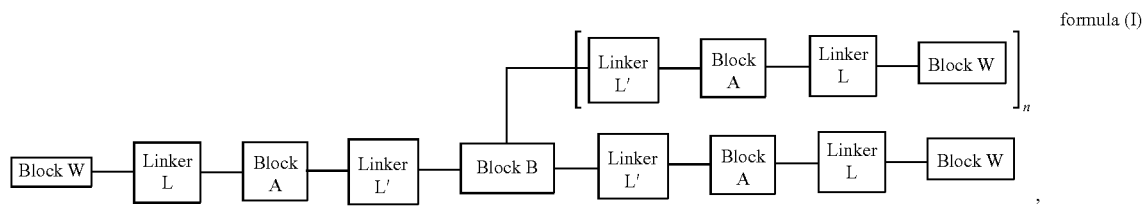

formula (I)

wherein n is an integer from 0 to 4 (e.g., n=1, 2, 3, or 4);

Block B comprises an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A comprises an optionally substituted $C_1$-$C_6$ alkylene, wherein Block A is derived from a diisocyanate crosslinker;

Block W comprises an optionally substituted $C_0$-$C_3$ alkyl-benzene-diol or optionally substituted $C_0$-$C_3$ alkyl-benzene-triol;

Linker L' comprises a carbamate; and

Linker L comprises a urea, wherein the adhesive composition has a tackifying temperature of at least 40° C. (e.g., at least 42° C., at least 45° C., at least 50° C., at least 55° C., or between from 40° C. to 55° C.).

In some embodiments, Block B comprises an oligomer derived from a polyester, polalkylene glycol, polysilicone, or polycarbonate. In particular embodiments, the Block B oligomer has a MW≤4,000 g/mol (e.g., 1±0.5 KDa, 2±0.5 KDa, or 3±1 KDa).

In some embodiments of the third aspect, the adhesive composition is not water soluble.

In some embodiments of the third aspect, the adhesive composition comprises a heat transfer agent (e.g., sodium chloride, iron(III) phosphate dihydrate, iron(III) citrate monohydrate, hydroxyapatite, tetracalcium phosphate, sodium carbonate, or a combination thereof (e.g., hydroxyapatite)). In some embodiments, the heat transfer agent is present in an amount that permits the softened adhesive composition to cool and harden in 120 seconds or less (e.g., 10 seconds or less). In some embodiments, the heat transfer agent is present in an amount that permits the adhesive composition to soften within 120 seconds or less of applying energy (e.g., 10 seconds or less). In some embodiments, the heat transfer agent comprises about 0.5-60% (w/w) of the adhesive composition (e.g., 7.5±2.5%, 10±5%, 15±5%, 20±5%, 25±10%, 37.5±5%, 50±10%, or 35-60% (w/w)).

In some embodiments of the third aspect, Block B has the structure of formula (II):

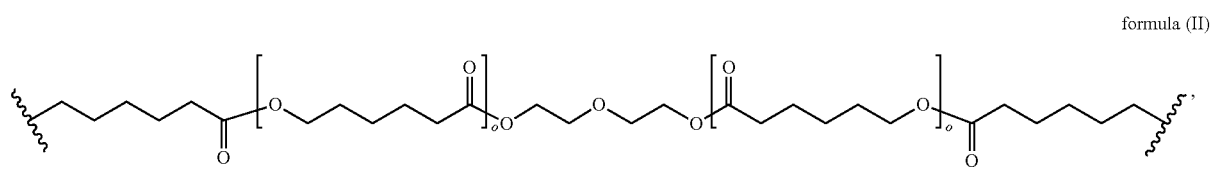

formula (II)

wherein each o is, independently, an integer from 0 to 20 (e.g., n=0-4, 2-6, 4-10, 5-15, or 10-20).

In some embodiments of the third aspect, Block B has the structure of formula (III):

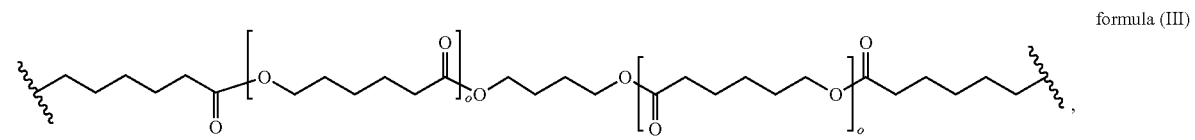

formula (III)

wherein each o is, independently, an integer from 0 to 20 (e.g., n=0-4, 2-6, 4-10, 5-15, or 10-20).

In some embodiments of the third aspect, Block B has the structure of formula (IV):

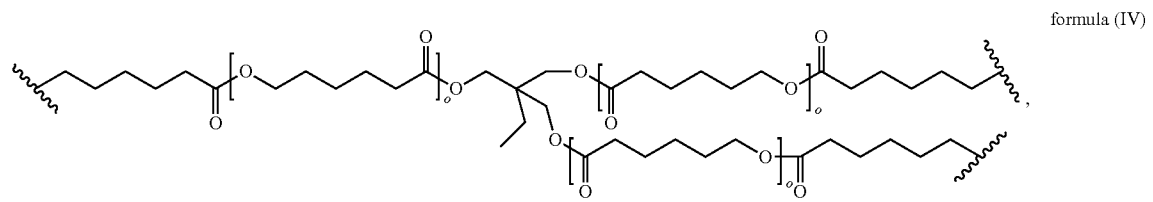

formula (IV)

wherein each o is, independently, an integer from 0 to 20 (e.g., n=0-4, 2-6, 4-10, 5-15, or 10-20).

In some embodiments of the third aspect, Block B has the structure of formula (V)

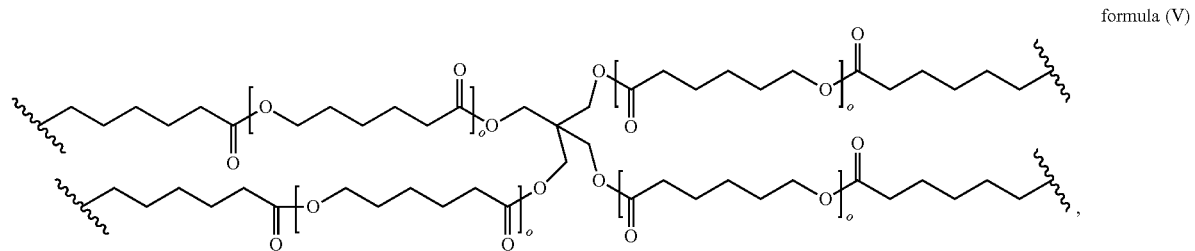

formula (V)

wherein each o is, independently, an integer from 0 to 20 (e.g., n=0-4, 2-6, 4-10, 5-15, or 10-20).

In some embodiments of the third aspect, Block B has the structure of formula (VI):

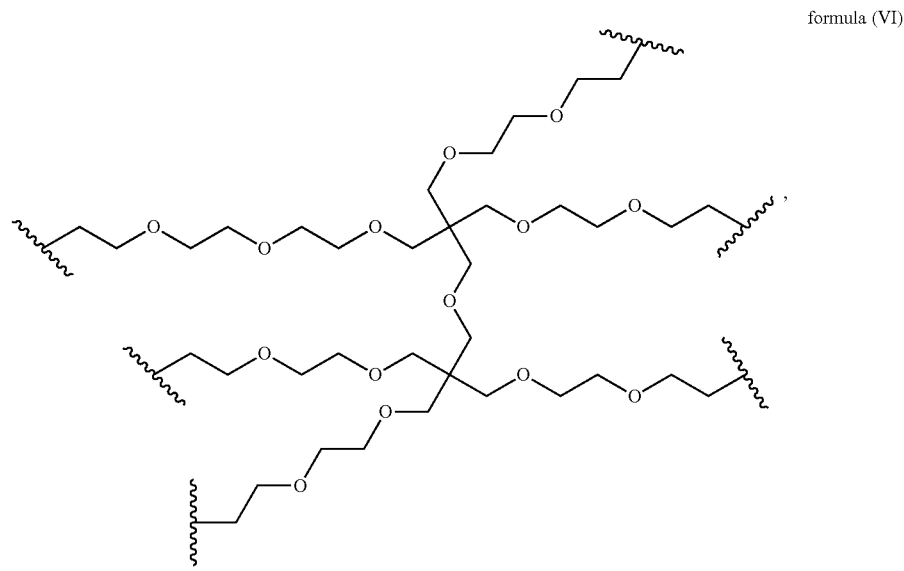 [SMILES: *CCOCCOCCOCC(COCCOCC*)(COCCOCC*)COCC(COCCOCC*)(COCCOCC*)COCCOCC*]

formula (VI)

wherein each o is, independently, an integer from 0 to 20 (e.g., n=0-4, 2-6, 4-10, 5-15, or 10-20).

In some embodiments of the third aspect, Block A has the structure of formula (VII):

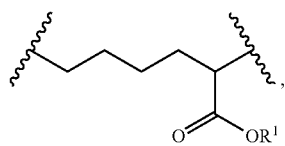

formula (VII)

wherein $R^1$ is $C_1$-$C_3$ alkyl.

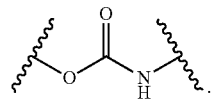 [SMILES: *NC(=O)O*]

In some embodiments of the third aspect, Linker L' has the structure:

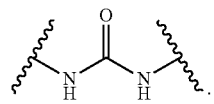

In some embodiments of the third aspect, Linker L has the structure:

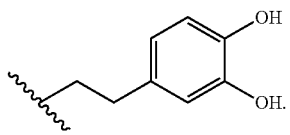 [SMILES: *CCc1ccc(O)c(O)c1]

In some embodiments of the third aspect, Block W has the structure:

In some embodiments of the third aspect, the filler comprises polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof, or a blend thereof. In some embodiments, the filler comprises polycaprolactone (PCL), polydioxanone (PDX), poly(lactic-co-glycolic acid) (PLGA), or poly-3-hydroxybutyrate (P3HB), or a copolymer thereof, or a blend thereof.

In a fourth aspect, the invention features a tape comprising (i) a non-adhesive polymeric top layer, and (ii) a bottom layer comprising the adhesive composition of any one of the preceding embodiments.

In some embodiments of the fourth aspect, the non-adhesive polymeric top layer comprises polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof.

Definitions

As used herein, the term "about" represents a value that is in the range of ±10% of the value that follows the term "about."

The term "adhesion section," as used herein, refers to a portion of a device of the disclosure containing an adhesive composition. For example, the adhesion section in the device of the invention can be composed of 30-100% (w/w) of one or more of an adhesive composition (e.g., a polymer having the structure of formula (I) described herein), 0-70% (w/w) of one or more of a filler (e.g., a non-adhesive polymer), and 0.5-60% (w/w) of one or more of a heat transfer agent. The adhesion section adheres to at least one of the objects (e.g., a bone fragment). The adhesion section may also be one side of the device (e.g., the adhesion side).

As used herein, the term "adhesion side" refers to a coating or layer that is comprised of the following: 1) one or more of an adhesive (e.g., preferably a plurality of adhesives); 2) one or more of a filler; and 3) one or more of a heat transfer agent. The adhesion side can be softened upon exposure to energy such as, e.g., infrared radiation, radiofrequency (RF)).

As used herein, the term "adhesive composition" refers compounds and blends that can adhesively affix one or more objects or materials together. The adhesive composition can be a polymer having the structure of formula (I), as described herein.

As used herein, the term "biocompatible" means the material will have no adverse effects on cells, tissue, or function in vivo for the indicated use.

As used herein, the term "biodegradable" means the material is capable of being broken down especially into innocuous products by the action of living things (e.g., the in vivo physiological environment). A biodegradable material may be hydrolysable or enzyme degradable.

The term, "filler," as used herein, refers to a non-adhesive material or substance that may be added to alter properties including, but not limited to, adhesion strength, tackifying temperature, cytotoxicity, tensile strength, time of rigidification, and viscosity. For example, a filler can be, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof.

As used herein, the term "heat transfer agent" is compound that accelerates the formation of a softened adhesive. A heat transfer agent may be a salt, such as, e.g., sodium chloride, iron(III) phosphate dihydrate, iron(III) citrate monohydrate, hydroxyapatite, tetracalcium phosphate, or sodium carbonate.

As used herein, the term "rigidify" refers to an increase in the stiffness of the material or substance. For example, an adhesion section (or adhesion side) of the disclosure can be softened after exposure to energy (e.g., within 120 seconds or less (e.g., within 10 seconds or less)); the adhesion section (or adhesion side) may then rigidify (i.e., stiffen) within 120 seconds or less (e.g., within 10 seconds or less). The rigidification of the adhesion section (or adhesion side) which fixes two (or more) bone fragments with respect to each other allows bone fractures to heal.

As used herein, the term "soften" refers to a decrease in the stiffness of the material or substance. For example, a device or an adhesion side of the disclosure can soften after exposure to energy; within 120 seconds or less (e.g., 10 seconds or less), the softened adhesion side can flow, conforming to the geometry of a biological tissue or other substrate.

As used herein, the term "tackifying temperature" refers to a temperature at which an adhesive blend or compound goes from non-flowable to string forming when contacted with a glass pipette tip. The adhesive blend or compound may decrease in stiffness (e.g., a reversible phase transition temperature). For example, a device or an adhesion side of the disclosure can soften once it reaches the tackifying temperature (e.g., the device or the adhesion side of the disclosure).

The term "subject," as used herein, refers to a human or non-human animal (e.g., a mammal such as a non-human primate, horse, cow, pig, or dog).

As used herein, the term "support structure" refers to a portion of a device of the disclosure that physically supports an adhesive section. For example, the device of the invention can be composed of 40-100% of one or more of a non-adhesive polymer (e.g., as a support). The support structure can be found between two adhesion sections. For example, the support structure can be one side of the device (e.g., the support side).

As used herein, the term "support side" refers to a support structure positioned as a backing for the adhesion side of a device of the invention. The support side can be formed from one or more non-adhesive polymers, such as, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof. For example, when the device is a bone tape, the support side can form a non-adhesive backing that structurally supports adhesion sections on the sticky side of the bone tape.

As used herein, the term "surface fouling" refers to an adhesive or admixture of two or more adhesives losing the ability to adhere to a surface in the presence of an aqueous liquid (e.g., water, blood, serum, plasma). The adhesion sections in the devices of the invention can be formulated to resist surface fouling.

The term "water soluble," as used herein, refers to a material or substance that may dissolve in water. A material or substance that is "not water soluble" (e.g., an adhesion section (or adhesion side) of the disclosure) refers to a material or substance in which less than 30 mg of the material or substance dissolves in 1 L of water at 25° C.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

Chemical Terms

It is to be understood that the terminology employed herein is for the purpose of describing particular embodiments and is not intended to be limiting.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, propyl, butyl, pentyl, and hexyl. Furthermore, where a compound includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). In some embodiments, an alkyl group is unbranched (i.e., is linear); in some embodiments, an alkyl group is branched. Alkyl groups are exemplified by methyl, ethyl, n- and iso-propyl, n-, sec-, iso- and tert-butyl, neopentyl, and the like.

As used herein, the term "alkylene" refers to a saturated divalent linker having a specified size (e.g., $C_{1-6}$ alkylene). They include straight-chain, branched-chain, and cyclic forms as well as combinations of these, containing only C and H when unsubstituted. Because they are divalent, they can link together two parts of a molecule. Examples are —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—. These groups can be substituted by the groups typically suitable as substituents for alkyl, groups as set forth herein.

As used herein, the terms "$C_0$-$C_3$ alkyl-benzene-diol" and "$C_0$-$C_3$ alkyl-benzene-triol" refer to substituents that optionally include an alkyl chain of 0 to 3 carbons in length that terminate in a benzene-diol or benzene-triol. The substituents can have the formula below:

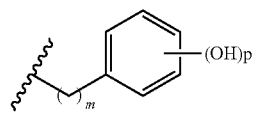

wherein m is 0, 1, 2, or 3; and p is 2 or 3.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional. In particular embodiments, a substitution is required by a given structure, and optionally substituted refers to one or more additional substituents. For example, in moiety -$L^2$-$R^4$ when $L^2$ is an alkyl the moiety describes an alkyl "$L^2$" that is substituted by group $R^4$. In some embodiments, the term optionally substituted X means that X may be optionally substituted with one or more (e.g., 1, 2, 3, 4, 5, or 6) substituents, which may independently be any of the substituents as described herein. Exemplary substituents include, without limitation, alkyl, hydroxyl, alkoxy, aryloxy, halogen, fluoroalkyl, carboxyl, carboxyalkyl, amino, aminoalkyl, monosubstituted amino, disubstituted amino, and quaternary amino groups including from 0 to 6 carbon atoms and from 0 to 4 heteroatoms selected from O, N, F, Cl, Br, and I. Substituents can include methyl, ethyl, carboxymethyl, acyl, $CF_3$, fluoro, and chloro.

DETAILED DESCRIPTION OF THE INVENTION

Figure 1:
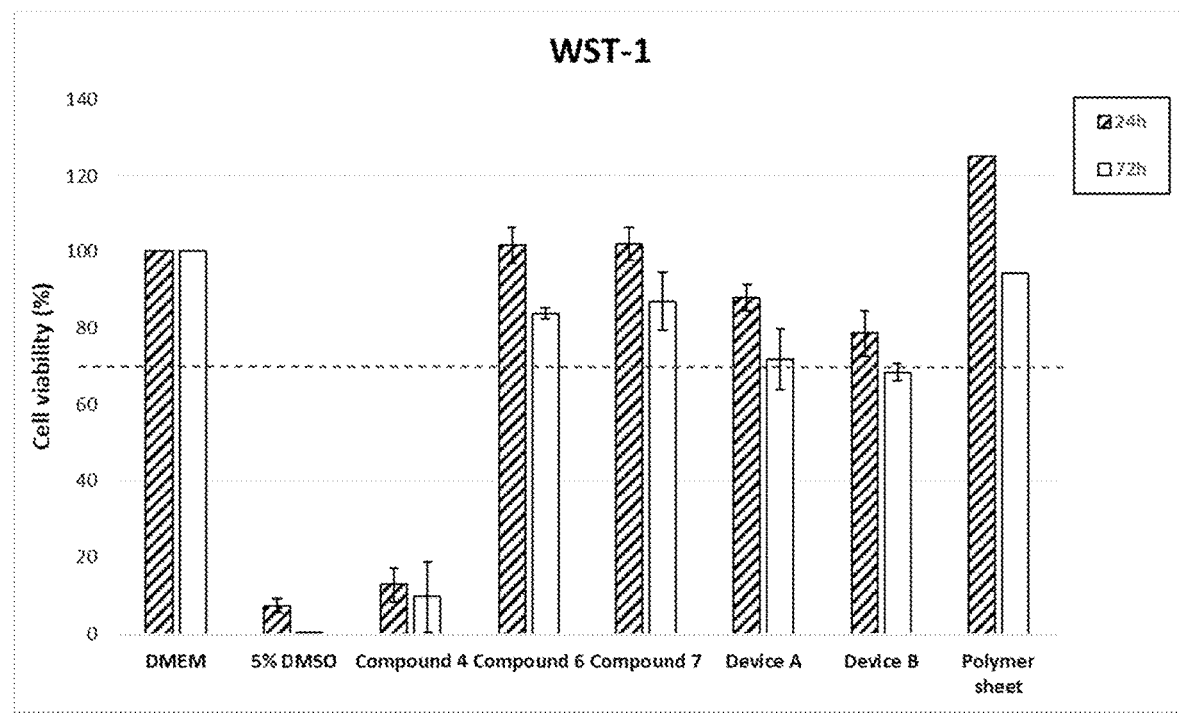
FIG. 1 is a graph showing cytotoxicity of materials in comparison to negative and positive controls (DMEM and 5% DMSO, respectively). Results are expressed as mean±standard deviation; n=4.

The disclosure features adhesive devices for holding objects (e.g., bone fragments) fixed with respect to each other. The disclosed device is useful for attaching to bone or to secure a material to a tissue in order to provide stability or support. The disclosed device may eliminate or reduce the need to use staples, sutures, tacks, screws, or the like to secure or repair damaged tissues (or bone), or to secure implants within the body.

Devices

A device of the disclosure can be used to hold two or more objects (e.g., bone fragments, ligaments, tendons) fixed with respect to each other. The device of the disclosure can be made of a gradient of a mixture of one or more adhesives (e.g., polymer(s) having the structure of formula (I) described herein) and one or more fillers (e.g., non-adhesive polymers).

Gradient of Adhesive(s), Filler(s), and Heat Transfer Agent(s)

The device of the disclosure may have varying compositions in different sections of the device. For example, the device can include at least two sections: (i) at least one adhesion section (e.g., a section of the device composed of: 30-100% (w/w) of one or more adhesives (e.g., polymer(s) having the structure of formula (I) as described herein), 0-70% (w/w) of one or more fillers (e.g., non-adhesive polymer(s)), and 0.5-60% (w/w) of one or more of heat transfer agent(s))) which adheres to at least one of the objects (e.g. tissues, such as, e.g., bone fragments, ligaments, tendons, etc.); and (ii) at least one support structure (e.g., a section of the device composed of: 40-100% (w/w) of one or more fillers (e.g., a non-adhesive polymer), and 0-60% (w/w) zero or more adhesives and zero or more heat transfer agents). The support structure may be formed from an anchoring material such as, e.g., polycaprolactone. The adhesion section (e.g., a section of the device composed of a sufficiently high amount of adhesive(s)) may be non-tacky at room temperature, and may be softened upon exposure to energy, such as, e.g., infrared radiation, or radiofrequency (RF)). The softened adhesion section can conform to the shape of the object (e.g., a bone fragment) it contacts. Once the energy exposure is ceased, the adhesion section will cool and rigidify, thus binding the object (e.g., a bone fragment) it contacts. The process may be repeated for the second object (and for the third, fourth, fifth object, or however many objects there are to secure to the preceding objects). This reversible softening feature of the adhesion section is advantageous so as to facilitate ease of handing, placement, workflow and control of device application.

The adhesion section and support structure may be arranged to make sides of the device: an adhesion side (where the adhesion section is a coating of one or more adhesives admixed with one or more fillers) can contact and adhere two or more objects (e.g., bone fragments), and a support side that backs the adhesion side. In this case, energy (e.g., infrared radiation, radiofrequency (RF)) may be delivered to the support side of the device through which heat can transfer to the adhesion side (which contacts the object(s)) without significant deformation of the support structure. This selective softening of the adhesive component relative to the support component is advantageous so as to retain the strength and/or performance of the support structure.

The adhesion section (or adhesion side) may be composed of an admixture of adhesives (e.g, polymer(s) having the structure of formula (I) as described herein) and fillers that may be varied to alter properties of the device of the disclosure such as, e.g., adhesion strength, tackifying temperature, cytotoxicity, tensile strength, time of rigidification, surface fouling resistant properties, brittleness, and viscosity.

The support structure (or support side) may be composed of an admixture of fillers and adhesives that may be varied to alter properties of the support, such as, e.g., porosity (e.g., having pores or texture in which an adhesive may fill), brittleness (e.g., the support structure (or support side) preferably can bend or twist 90° without flaking), flexibility, surface fouling properties, and tensile strength.

A device (and its components, e.g., the adhesive polymers and non-adhesive polymers that make up the adhesion section (and adhesion side) and support structure (and support side)) of the disclosure may be optionally biodegradable and optionally biocompatible. Furthermore, the device (and its components described herein) may be optionally bioresorbable.

Adhesives of the Disclosure

A device of the disclosure may contain a mixture of one or more adhesives having the structure of formula (I):

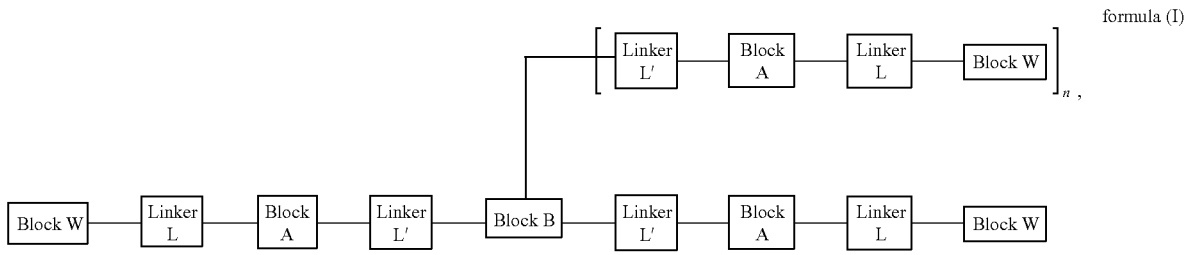

formula (I)

where n is an integer from 0 to 4 (e.g., n=1, 2, 3, or 4);

Block B is an oligomer derived from a polyester, polyether, polalkylene glycol, polysilicone, or polycarbonate with a MW<10,000 g/mol (e.g., 2±1 KDa, 4±2 KDa, 5±2.5 KDa, or 8±2 KDa);

Block A comprises an optionally substituted $C_1$-$C_6$ alkylene, wherein Block A is derived from a diisocyanate crosslinker;

Block W comprises an optionally substituted $C_0$-$C_3$ alkyl-benzene-diol or optionally substituted $C_0$-$C_3$ alkyl-benzene-triol;

Linker L' comprises a carbamate; and

Linker L comprises a urea.

In some embodiments, Block B comprises an oligomer derived from a polyester, polalkylene glycol, polysilicone, or polycarbonate. In particular embodiments, the Block B oligomer has a MW≤4,000 g/mol (e.g., 1±0.5 KDa, 2±0.5 KDa, or 3±1 KDa).

Block B can have the structure of formula (II), formula (III), formula (IV), formula (V), or formula (IV):

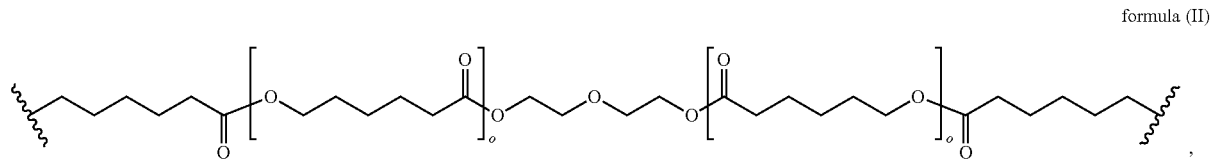

formula (II)

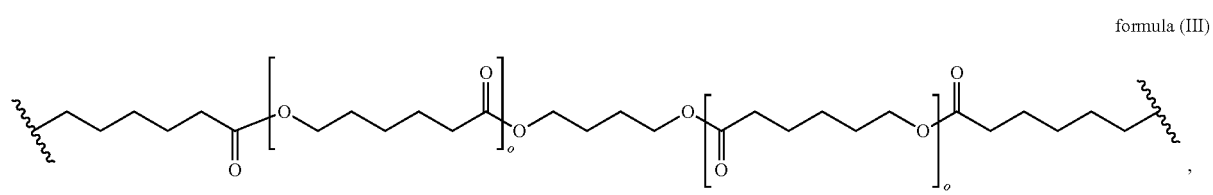

formula (III)

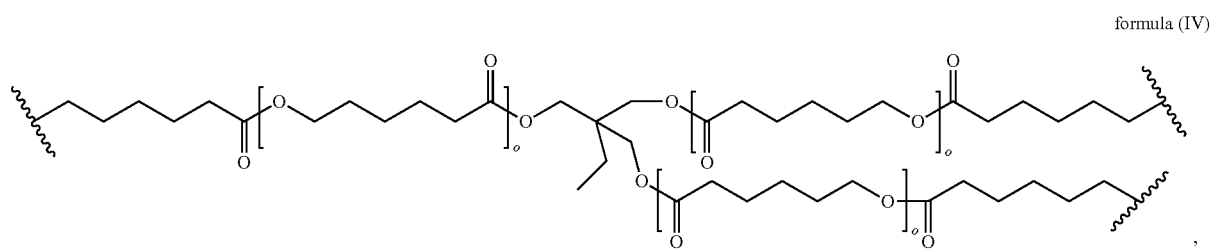

formula (IV)

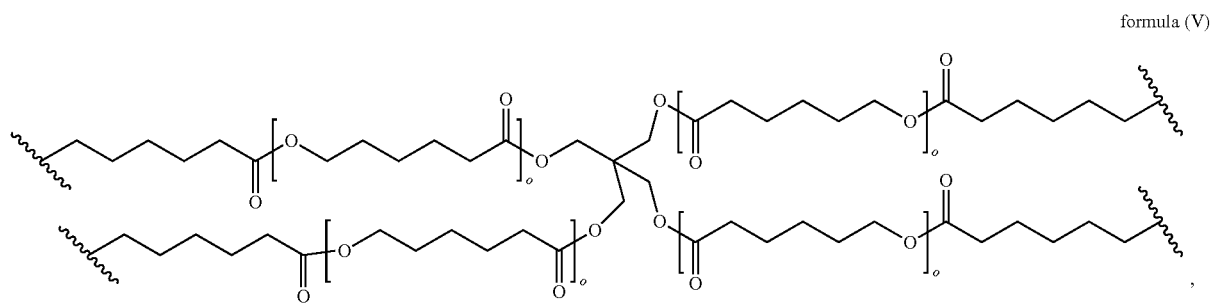

formula (V)

-continued

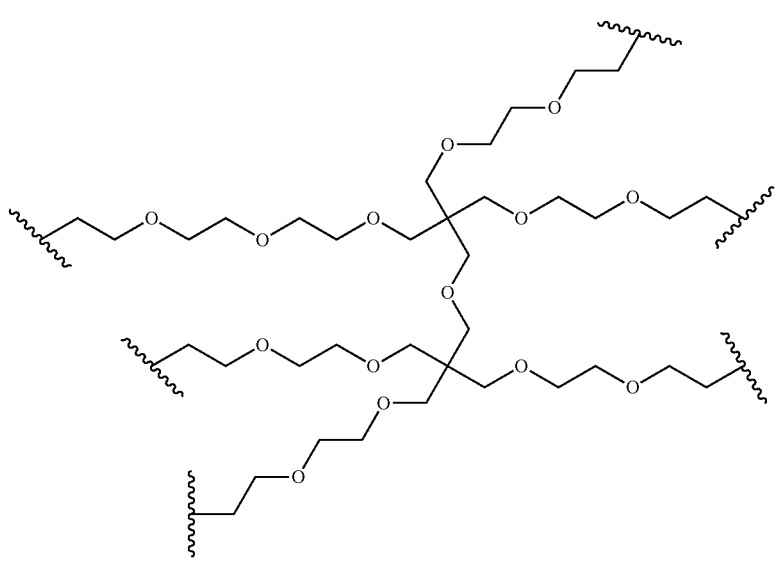

formula (VI)

where each o is, independently, an integer from 0 to 20 (e.g., n=0-4, 2-6, 4-10, 5-15, or 10-20).

Block A can have the structure of formula (VII):

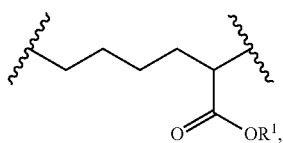

formula (VII)

where $R^1$ is $C_1$-$C_3$ alkyl.

Linker L' can have the structure:

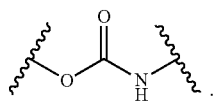

Linker L can have the structure:

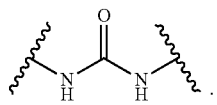

Block W can have the structure:

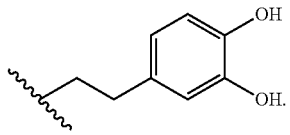

The isolated adhesive compound can have a tackifying temperature of at least 10° C., at least 15° C., at least 20° C., at least 25° C., or between from 10° C. to 55° C. Blended materials containing an adhesive compound can have a tackifying temperature at least 40° C. (e.g., at least 42° C., at least 45° C., at least 50° C., at least 55° C., or between from 40° C. to 55° C.).

An adhesive or admixture of adhesives of the disclosure may be optionally biodegradable and optionally biocompatible. Furthermore, the adhesive or admixture of adhesives may be optionally bioresorbable. An adhesive or admixture of adhesives of the disclosure can have water solubilities less than 30 mg per L of water.

Generally, adhesives for use in biomedical devices as found in the prior art all teach of the assembly of irreversible crosslinked networks by virtue of large polymeric assemblies either use or are formed chemically from the monomers (e.g. US20140311673A1, WO2017044896A1, WO2014158288A1, US20120029559A1, US20160346424A1, WO2016134304A1, PCT/CA2020051781). They either teach that low molecular weight molecules with low viscosity must be used for flowing before cure or, when large solid polymeric materials are used, solvents or other diluents are necessary to make them flowable. The use of solvents in biomedical adhesives, however, introduces unnecessary toxicity and/or impedes the curing and bonding of the adhesive. Further, flowable systems are susceptible to runoff or leaching of reactive adhesive components and/or oxidants away from the site of application, and/or retention of unreacted species, all of which can present as inflammatory responses in vivo.

Compared to the prior art, the adhesives of formula I are not dependent upon in situ curing reactions for adhesion, and are not susceptible to adhesive leaching/runoff from the application site which can result in undesired side reactions and inflammatory complications. Further, the nature of Block B also means that these adhesives are not particularly prone to swelling and, therefore, inflammatory complications due to the swelling of the device in vivo. The reversible softening properties of the adhesives at temperatures close to physiological temperatures also introduces the benefits of not requiring solvent for surface wetting, of being non-tacky at room temperature, thereby facilitating facile workflow, and of not requiring high temperatures for adhesive softening so as to mitigate the risk of tissue necrosis.

Filler

A device of the disclosure can contain a varying amount (or gradient) of one or more fillers. A filler can be non-adhesive materials or substances that may be added to alter properties of the device of the disclosure such as, e.g., adhesion strength, tackifying temperature, cytotoxicity, tensile strength, time of rigidification, and viscosity. For example, a filler can be, e.g., polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof. Preferably, the support structure (or support side) can contain one or more of polycaprolactone (PCL), polydioxanone (PDX), poly(lactic-co-glycolic acid) (PLGA), or poly-3-hydroxybutyrate (P3HB), and a copolymer thereof. More preferably, the support structure will present a melting temperature at least 20° C. higher than that of the adhesive component (e.g., at least 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C. higher than that of the adhesive component). Even more preferably, the support structure will present a melting temperature of at least 100° C. higher than that of the adhesive component.

A filler or admixture of fillers of the disclosure may be optionally biodegradable and optionally biocompatible. Furthermore, the filler or admixture of fillers may be optionally bioresorbable.

Heat Transfer Agent

An adhesion section (or adhesion side) can contain one or more of a heat transfer agent (e.g., a compound that may accelerate the formation of a softened adhesive) in the adhesion section or the adhesion side of the device. The heat transfer agent may be a salt, such as, e.g., sodium chloride, iron(III) phosphate dihydrate, iron(III) citrate monohydrate, hydroxyapatite, tetracalcium phosphate, or sodium carbonate.

Softening and Rigidification of the Device

An adhesion section (or adhesion side) can reversibly soften (e.g., decrease in stiffness) or rigidify (e.g., increase in stiffness) when exposed to energy (e.g., infrared radiation, radiofrequency (RF)) or when cooled (e.g., cooling at ambient temperature without exposure to the energy described herein), respectively. The adhesion section (or adhesion side) is softened if the adhesive or admixture of adhesives has undergone a phase transition from solid to softened state (rigid to malleable state), and can form strings of softened polymer when contacted with a glass pipette tip. Once softened, the adhesion section (or adhesion side) can be contacted with one or more of the objects to be affixed. The softened adhesion section (or adhesion side) can subsequently rigidify within 120 seconds (or less) (e.g, less than 10 seconds) once the adhesion section (or adhesion side) is no longer exposed to energy (e.g., infrared radiation, RF). Preferably, the disclosed adhesion section (or adhesion side) has a tackifying temperature of 40° C. or greater.

Dimensions of the Device

The device of the disclosure may have a thickness between 0.02-1.5 mm (e.g., 0.3±0.2 mm). Depending on the application and mass of the tissue/bone to be stabilized, this thickness will vary accordingly. For example, a thinner device may be used for soft tissue applications (e.g., 0.05 mm thick) whereas a thicker device may be used for bone stabilization (e.g., 1.0 mm thick). Accordingly, the time required to soften the adhesion section (or adhesion side) will be proportional to the thickness of the device. Furthermore, the time required to rigidify will also be proportional to the thickness of the device.

The device of the disclosure may be prepared as a sheet (having all the components of a device described herein (e.g., an adhesion section, a support structure)) up to 100 mm long and 100 mm wide (e.g., 60 mm×60 mm). The sheet can be cut to any dimension and shape (e.g., 10 mm×40 mm) having a thickness as described herein.

Surface Fouling Resistant Properties

The device (specifically, the adhesion section(s) or adhesion side) of the disclosure can resist surface fouling in the presence of aqueous media (e.g., blood). The adhesive or the admixture of adhesives described herein can bind to objects (e.g., tissues that are wet or dry) as described herein. Once bound, the adhesive or the admixture may remain bound to the object(s) in the presence of aqueous media (e.g., blood). For example, a device of the disclosure can bind two (or more) objects in the presence of blood (e.g., horse blood or sheep blood).

Uses and Methods of Treatment

The disclosed device is useful for attaching to objects (e.g., bone), or to secure an object to another object (e.g., a material to a tissue) in order to provide stability or support. The disclosed device may eliminate or reduce the need to use staples, sutures, tacks, screws, or the like to secure or repair damaged tissues (or bone), or to secure implants within the body.

Attaching to Bone

The device of the disclosure may be useful for holding bone fragments (e.g., bone fragments in or from a subject) fixed with respect to each other.

Two or more bone fragments may be adhered (and thus secured) to one or more of the device disclosed herein. A bone fragment may be contacted with an adhesion section (or adhesion side) of the device. Another bone fragment may be in contact with the same adhesion section (or adhesion side), or a second adhesion section of the device. The contacted adhesion section may then be softened using an energy source such as, e.g., infrared radiation, radiofrequency (RF). After cooling, the adhesion section will solidify and bind to the bone fragment. The process may then be repeated for each adhesion section and bone fragment contact area. The bound device can thus stabilize the fracture, and maintain physiological alignment necessary for bone union. The process may also be done in situ or ex situ (e.g., a fragment may be removed from the body, contacted, and bonded with an adhesion section (or adhesion side) of the device, then put back in place and further secured), The device of the disclosure may hold two or more (e.g., 2 to 5, 6 to 10, 11 to 15, 16 to 20, 21 to 25, 26 to 30, 31 to 35, 36 to 40, 41 to 45, 46 to 50 or more) bone fragments fixed with respect to each other. The bone fragments may be fixed with respect to each other with at least one device. In some cases, two or more (e.g., 2 to 5, 6 to 10, 11 to 15, 16 to 20, 21 to 25, 26 to 30, 30 to 40, 40 to 50 or more) of the disclosed device may be used to hold two or more bone fragments fixed with respect to each other.

The device of the disclosure may be used in combination with current standards of care, such as, e.g., stabilizing conventional plates, holding communitions or scaffolds in place in load bearing regions.

Tissue Scaffold

The device of the disclosure can be used to hold a tissue scaffold or filler material in place within a defect in order to allow for regeneration to occur.

Attaching to a Previously Applied Device

The device of the disclosure may be used for attaching to objects (e.g., bone), or to secure an object to another object (e.g., a material to a tissue) by applying an additional device over a previously applied device of the disclosure to increase the rigidity of the fixation.

EXAMPLES

The examples described herein serve to illustrate the present invention, and the invention is not limited to the examples given.

ABBREVIATIONS

DSC differential scanning calorimetry
DMAc dimethylacetamide
DMSO dimethylsulfoxide
h hour(s)
LDI Ethyl Ester L-Lysine Diisocyanate
min minute(s)
MW molecular weight
mL milliliter(s)
MS mass spectrometry
m/v mass/volume
NMR nuclear magnetic resonance
PCL polycaprolactone
PDX polydioxanone
TEA triethylamine
TGA thermogravimetric analysis
THF tetrahydrofuran Example 1. Synthesis of Adhesives Compound 1

Compound 1 was synthesized via a 3-stage 1-pot method under $N_2$ atmosphere (Scheme 1). The PCL polyol (polycaprolactone diol; MW 1250 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 2.1 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was allowed to proceed overnight. The reaction was filtered to remove triethylamine hydrochloride by-product, and the resulting filtrate was stirred in a large excess (~10× volume of the reaction) of ether overnight to precipitate the adhesive. The supernatant was decanted and the precipitated adhesive was subsequently redissolved in a minimum volume of hot acetone/ethanol (90:10 v/v) and reprecipitated by solvent exchange centrifugation with ether (×3; 1:9 v/v). Compound 1 was obtained as a white crystalline powder after extended drying under vacuum at room temperature (n is about 5 (average)). 100% dopamine functionalization was observed by $^1$H-NMR.

Scheme 1: Synthesis of polycaprolactone diol-derived adhesive, Compound 1.

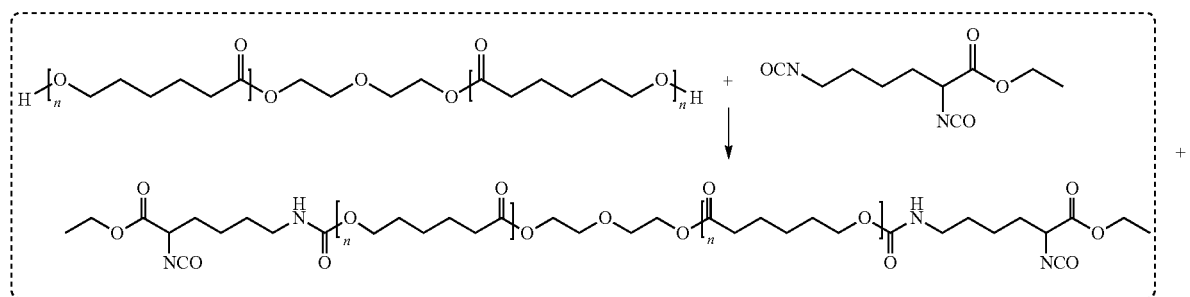

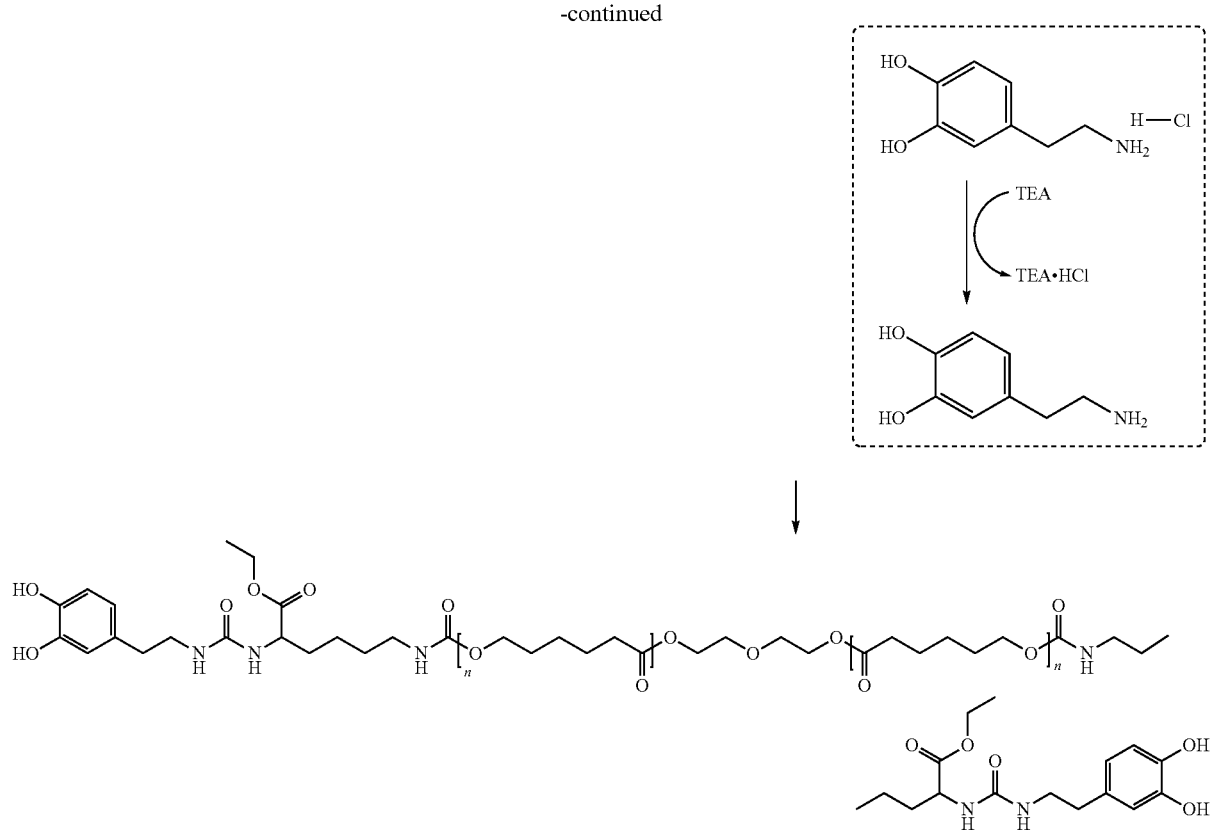

Compound 2

Compound 2 was synthesized via a 3-stage 1-pot method under $N_2$ atmosphere (Scheme 2). The PCL polyol (polycaprolactone diol; MW 2000 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 2.1 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was allowed to proceed overnight. Upon completion, the reaction mixture was filtered to remove the triethylamine hydrochloride by-product. The adhesive was then precipitated by solvent exchange centrifugation with ether (×3; 1:9 v/v), then filtered under vacuum. The adhesive was then redissolved in a minimum volume of hot acetone/ethanol (90:10 v/v) and reprecipitated as described above with ether. Compound 2 was obtained as a hard white waxy solid after extended drying under vacuum at room temperature (n is about 8.3 (average)). $^1$H-NMR analysis of Compound 2 demonstrated 73% dopamine functionalization.

Scheme 2: Synthesis of polycaprolactone diol-derived Compound 2

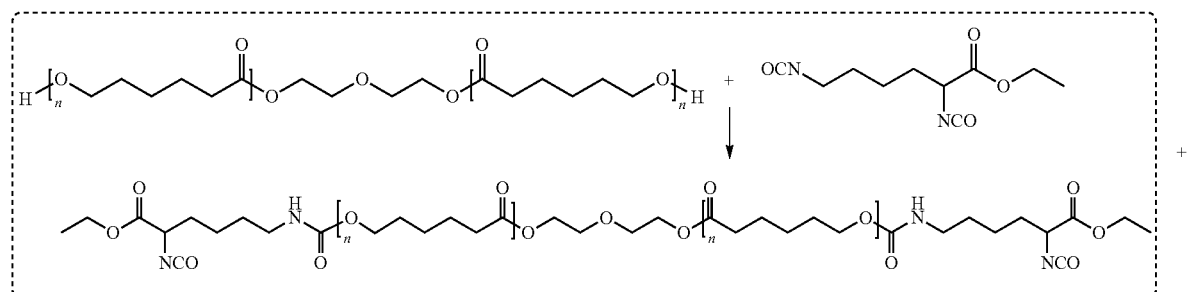

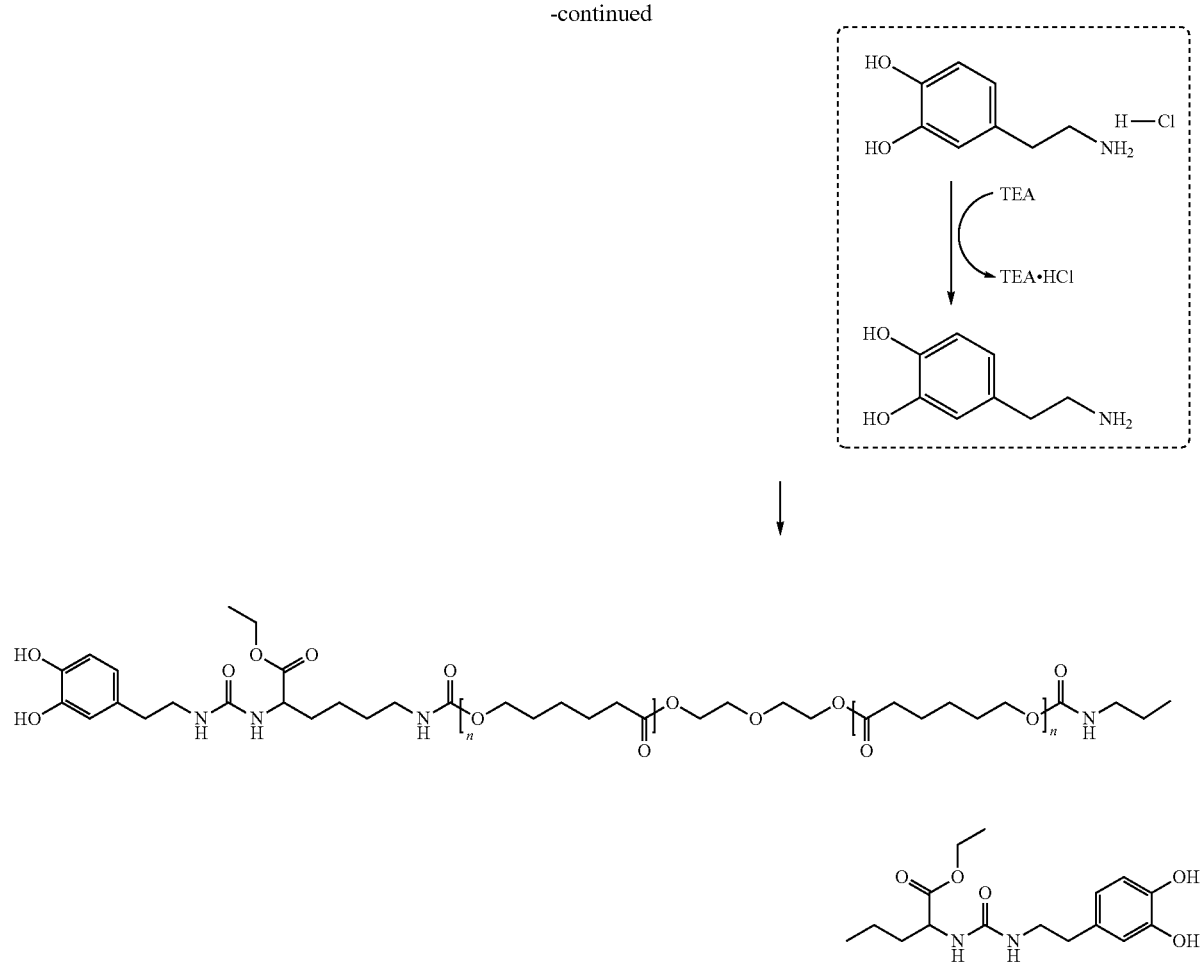

Compound 3

Compound 3 was synthesized via a 3-stage 1-pot method under $N_2$ atmosphere (Scheme 3). The PCL polyol (polycaprolactone diol; MW 4000 g/mol) was dried in a 2-necked round bottom flask for 2 h at 100° C. under vacuum, then dissolved in DMAc solvent (~1:5 m/v ratio) and allowed to cool to room temperature under $N_2$ atmosphere. 2 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (2 molar equivalents) was then added into the reaction and stirred until it was fully dissolved. The reaction was placed in an ice bath, and triethylamine (TEA; 2 molar equivalents) was added dropwise. The reaction was then removed to room temperature and allowed to proceed overnight. Upon completion, the adhesive was precipitated by stirring in a large excess (~10× volume of reaction) of acidified water. The adhesive was then filtered over vacuum and washed with copious amounts of distilled water until the filtrate was no longer acidic. Compound 3 was obtained as a fluffy white powder after extended freeze drying (n is about 17 (average)). $^1$H-NMR analysis of Compound 3 demonstrated 82% dopamine functionalization.

Scheme 3: Synthesis of polycaprolactone diol-derived Compound 3.

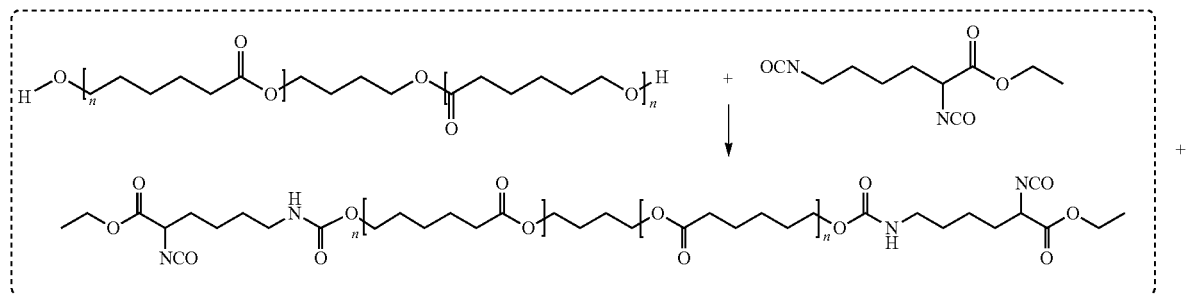

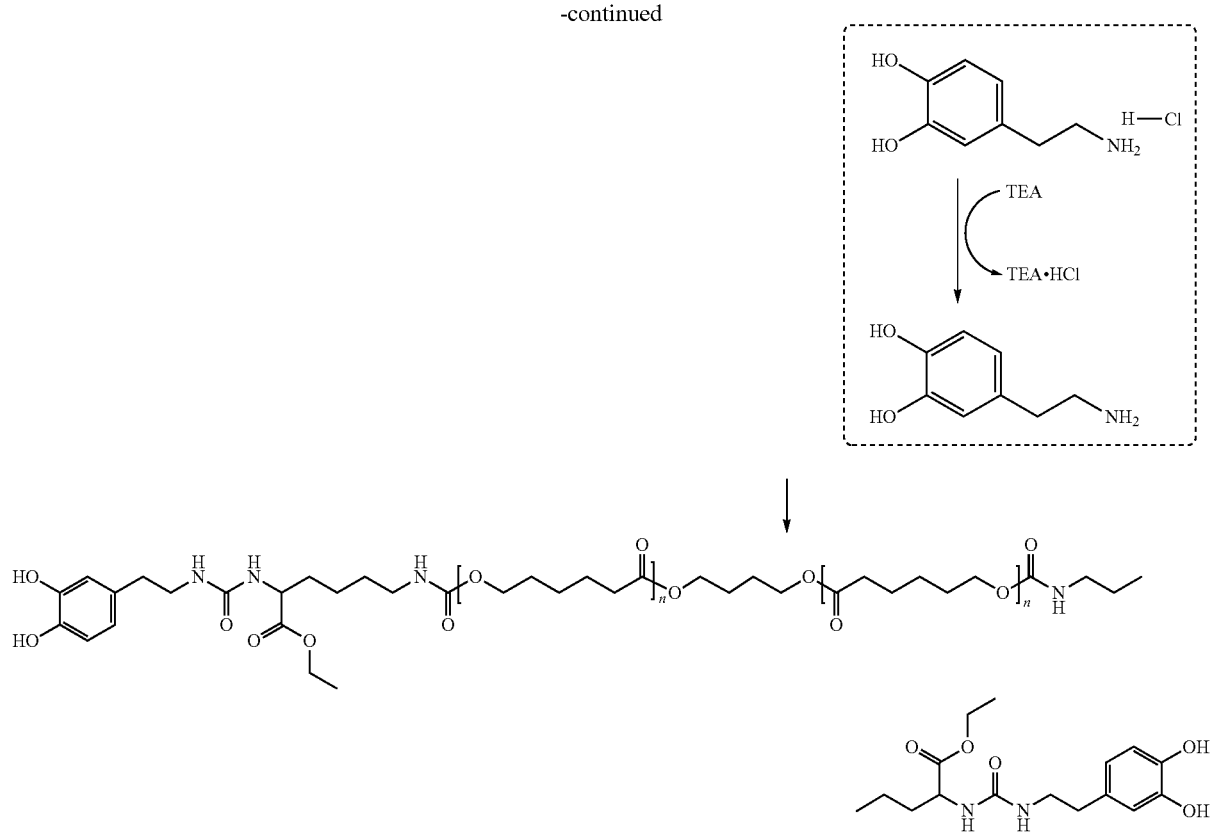

Compound 4

Compound 4 was synthesized via a 3-stage 1-pot method under $N_2$ atmosphere (Scheme 4). The PCL polyol (polycaprolactone triol; MW 300 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 3 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (3.1 molar equivalents) was then added into the reaction and stirred until it was fully dissolved. The reaction was placed in an ice bath, and triethylamine (TEA; 3 molar equivalents) was added dropwise. The reaction was allowed to proceed overnight. Upon completion, the reaction was filtered to remove the triethylamine hydrochloride residue and the adhesive was precipitated by solvent exchange centrifugation with acidified water (×1; 1:3 v/v). The adhesive was then washed, via solvent exchange centrifugation, with water until neutral (1:4 v/v) and ether (×4; 1:9 v/v). The adhesive was redissolved in a minimum volume of hot acetone/ethanol (90:10 v/v) and was reprecipitated by solvent exchange centrifugation with ether (×3; 1:9 v/v). Compound 4 was finally obtained as a white crystalline powder after extended drying under vacuum at room temperature (n is about 0.5 (average)). $^1$H-NMR analysis of Compound 4 demonstrated 80% dopamine functionalization.

Scheme 4: Synthesis of polycaprolactone triol-derived Compound 4.

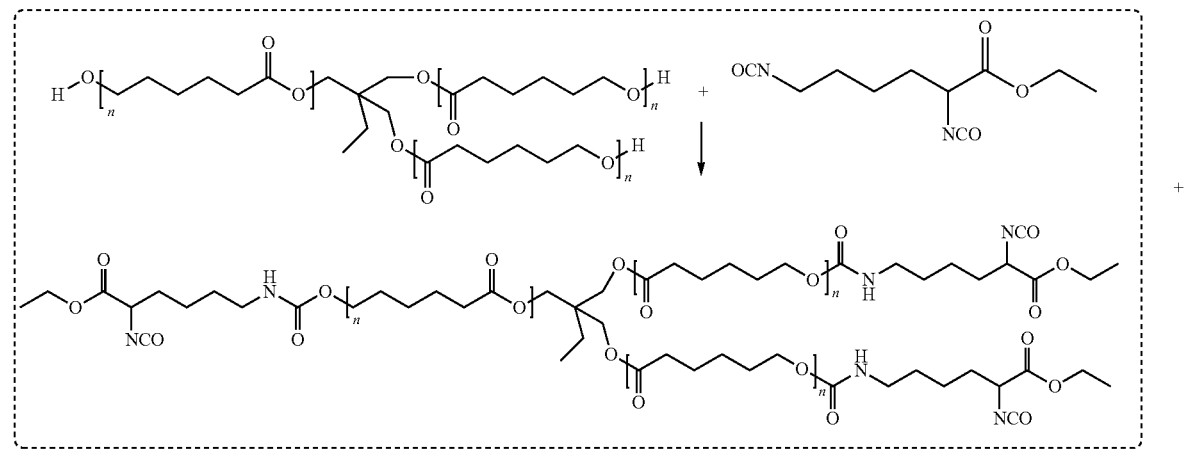

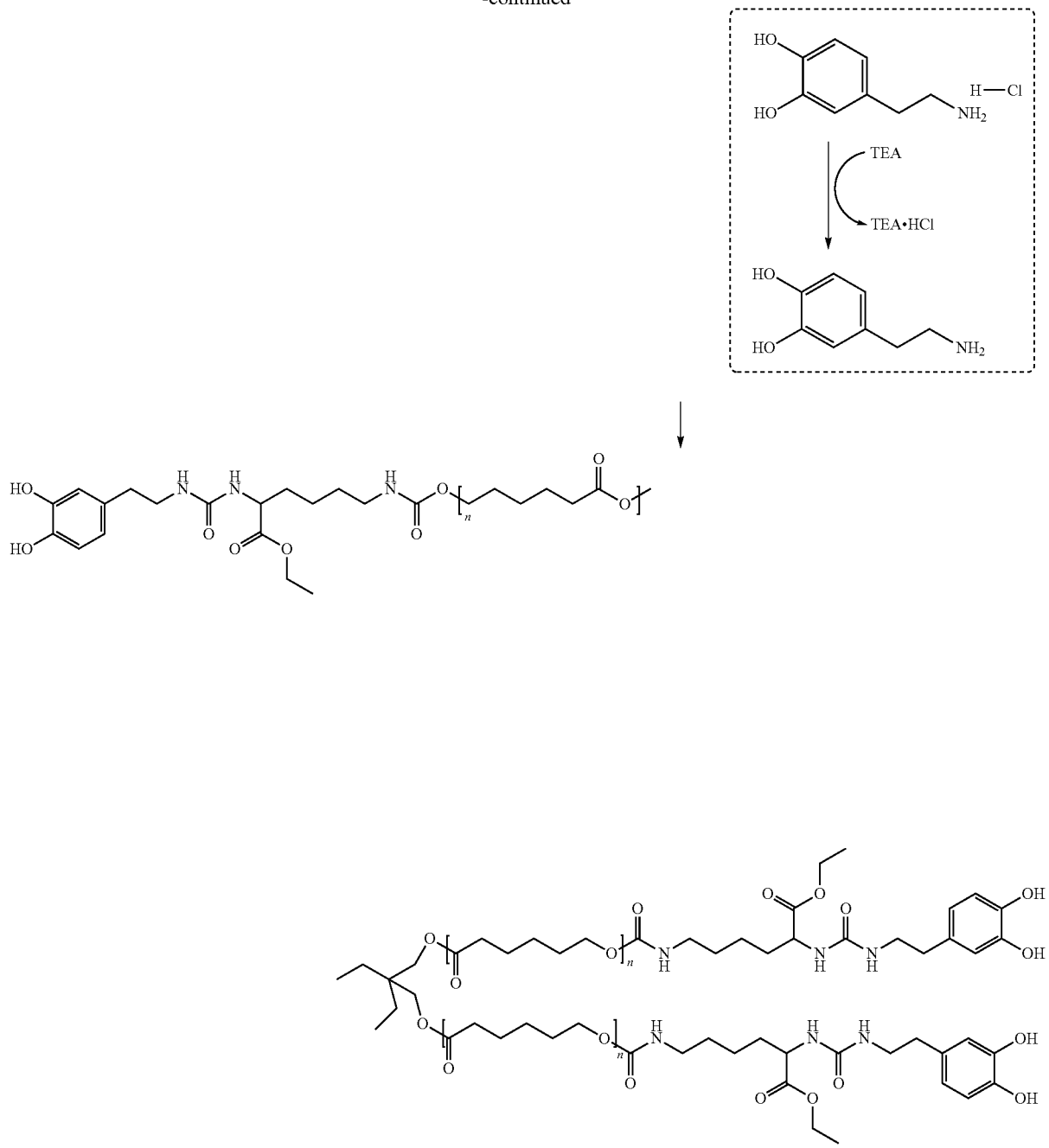

Compound 5

Compound 5 was synthesized via a 3-stage 1-pot method under $N_2$ atmosphere (Scheme 4). The PCL polyol (polycaprolactone triol; MW 900 g/mol) was dried in a 2-necked round bottom flask for 2 h at 75° C. under vacuum, then dissolved in DMAc solvent (~1:5 m/v ratio) and allowed to cool to room temperature under $N_2$ atmosphere. 3.1 molar equivalents of LDI (Ethyl Ester L-Lysine Diisocyanate) was added, and the reaction stirred at room temperature for 1 h, ramped to 75° C. over 2 h, held at 75° C. for 1 h, and finally stirred at room temperature overnight. Dopamine hydrochloride (3 molar equivalents) was then added into the reaction and stirred until it was fully dissolved. The reaction was placed in an ice bath, and triethylamine (TEA; 3 molar equivalents) was added dropwise. The reaction was allowed to proceed overnight. Upon completion, the reaction was filtered to remove the triethylamine hydrochloride residue and the adhesive was precipitated by solvent exchange centrifugation with acidified water (×1; 1:3 v/v). The adhesive was then washed, via solvent exchange centrifugation, with water until neutral (1:4 v/v) and ether (×4; 1:9 v/v). The adhesive was redissolved in a minimum volume of hot acetone/ethanol (90:10 v/v) and was reprecipitated by solvent exchange centrifugation with ether (×3; 1:9 v/v). Compound 5 was finally obtained as a pale yellow hard glassy solid after extended drying under vacuum at room temperature (n is about 2.3 (average)). $^1$H-NMR analysis of Compound 5 demonstrated 77% dopamine functionalization.

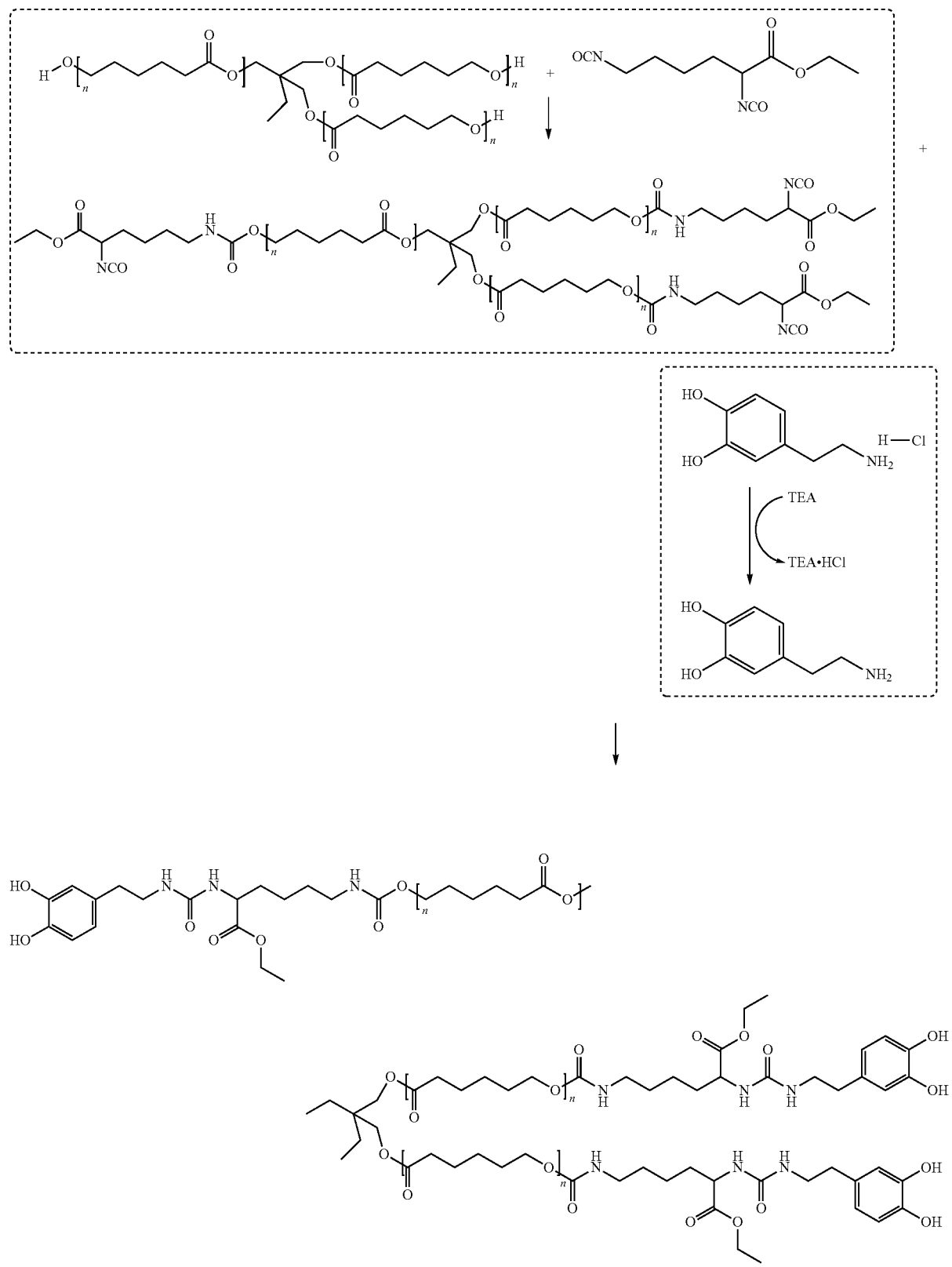
Scheme 5: Synthesis of polycaprolactone triol-derived Compound 5.

Compound 6

Compound 6 was synthesized via a 3-stage 1-pot method under $N_2$ atmosphere (Scheme 6). The PCL polyol (polycaprolactone triol; MW 2000 g/mol) was dried in a 2-necked round bottom flask for 2 h at 85° C. under vacuum, then dissolved in DMAc solvent (~1:5 m/v ratio) and allowed to cool to room temperature under $N_2$ atmosphere. 3 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (3.1 molar equivalents) was then added into the reaction and stirred until it was fully dissolved. The reaction was placed in an ice bath, and triethylamine (TEA; 3 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (×1; 1:3 v/v). The adhesive was then washed, via solvent exchange centrifugation, with water until neutral (1:4 v/v) and ether (×4; 1:9 v/v). The resulting adhesive was subsequently redissolved in a minimum volume of hot acetone/ethanol (90:10 v/v) and reprecipitated by solvent exchange centrifugation with ether (×4; 1:9 v/v) before being dried for an extended period under vacuum at room temperature to give Compound 6 as a white fluffy powder (n is about 5.5 (average)). $^1$H-NMR analysis demonstrated 90% dopamine functionalization.

Scheme 6: Synthesis of polycaprolactone triol-derived Compound 6.

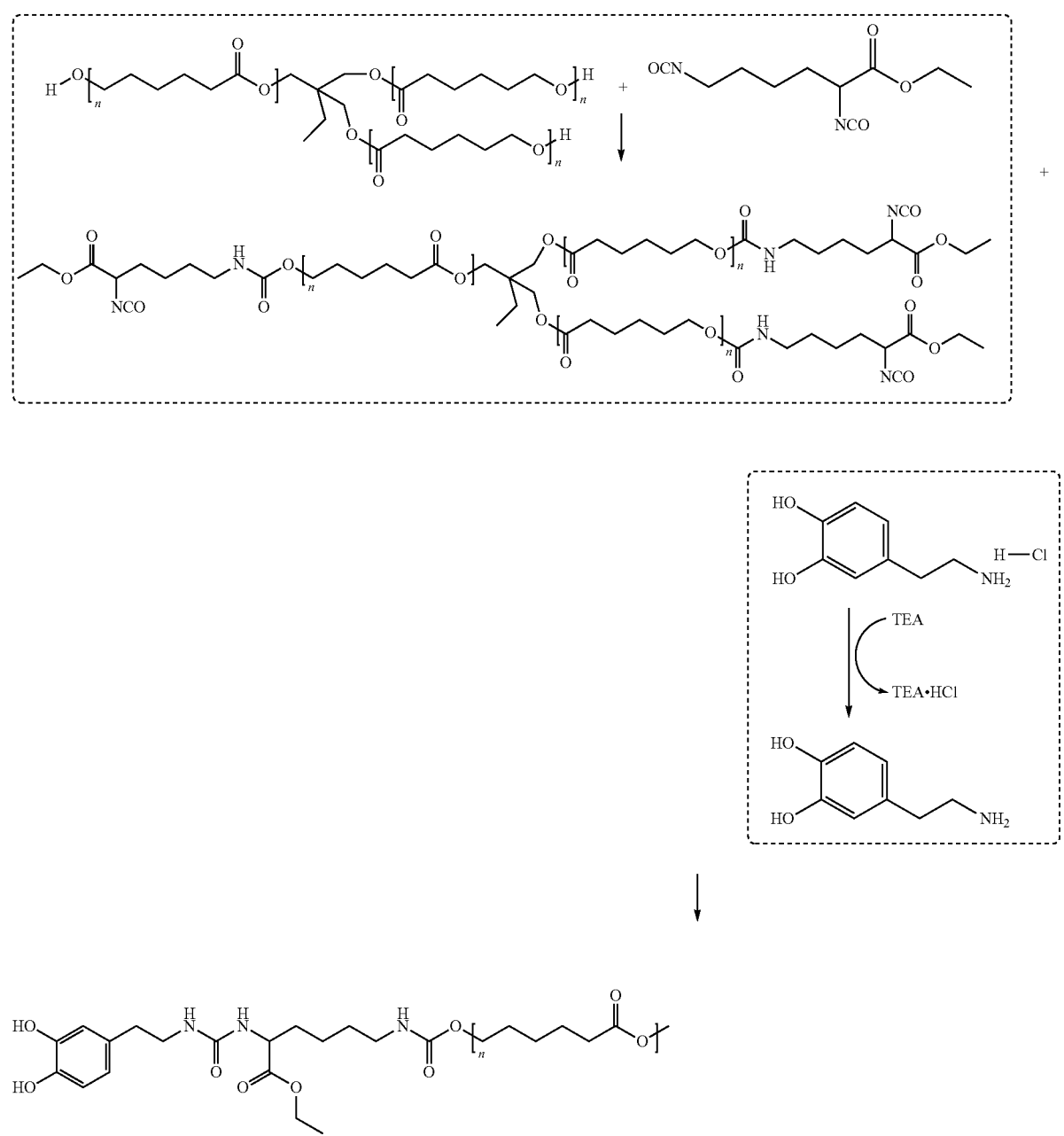

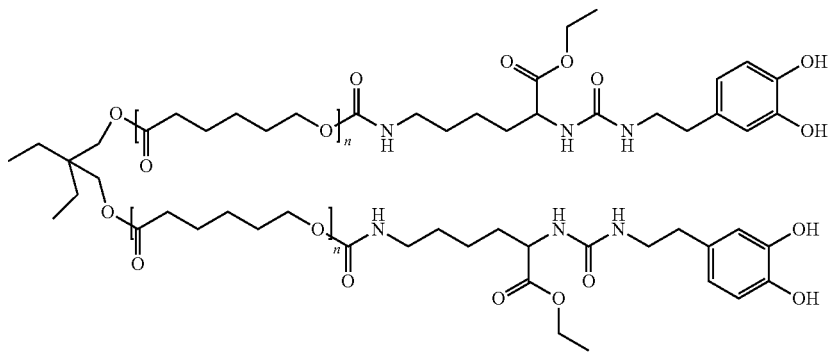

Compound 7

Compound 7 was synthesized via a 3-stage 1-pot method under $N_2$ atmosphere (Scheme 7). The PCL polyol (polycaprolactone tetrol; MW 1000 g/mol) was dried in a 2-necked round bottom for 2 h at 75° C. under vacuum, then dissolved in DMAc solvent (~1:5 m/v ratio) and allowed to cool to room temperature under $N_2$ atmosphere. 4 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (4.1 molar equivalents) was then added into the reaction and stirred until it was fully dissolved. The reaction was placed in an ice bath, and triethylamine (TEA: 4 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (×1; 1:3 v/v). The adhesive was then washed, via solvent exchange centrifugation, with water until neutral (1:4 v/v) and ether (×4; 1:9 v/v). The resulting adhesive was subsequently redissolved in a minimum volume of hot acetone/ethanol (90:10 v/v) and reprecipitated by solvent exchange centrifugation with ether (×4; 1:9 v/v) before being dried for an extended period under vacuum at room temperature to provide Compound 7 as a white spongy solid (n is about 1.9 (average)). $^1$H-NMR analysis demonstrated 89% dopamine functionalization.

Scheme 7: Synthesis of polycaprolactone tetrol-derived Compound 7.

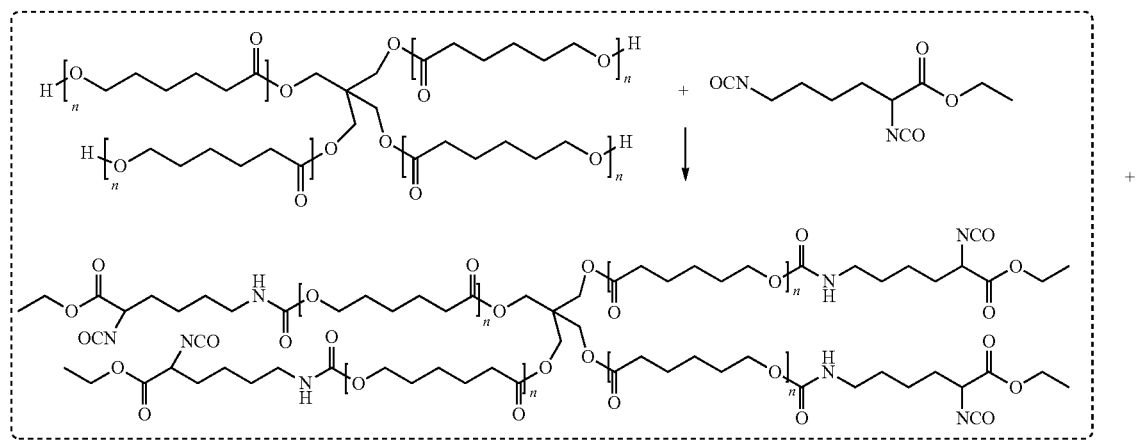

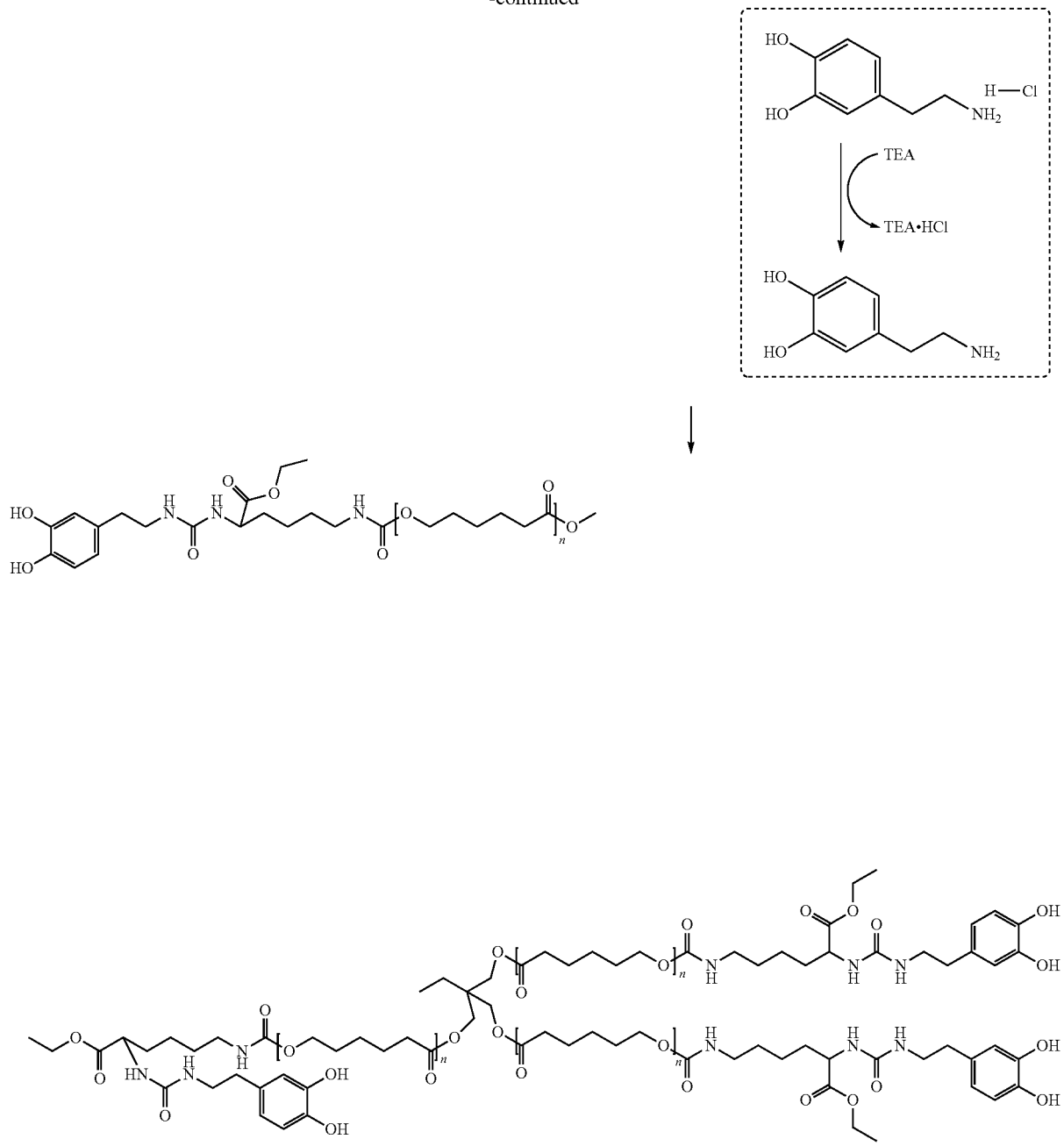

Compound 8

Compound 8 was synthesized via a 3-stage 1-pot method under $N_2$ atmosphere (Scheme 8). The PEE polyol (polyethylether hexol; MW 815 g/mol) was dried in a 2-necked round bottom for 2 h at 75° C. under vacuum, then dissolved in DMAc solvent (~1:5 m/v ratio) and allowed to cool to room temperature under $N_2$ atmosphere. 6 molar equivalents of LDI (Ethyl Ester L-Lysine Diisocyanate) was added, and the reaction was stirred at room temperature for 1 h, ramped to 75° C. over 2 h, held at 75° C. for 1 h, and finally stirred at room temperature overnight. Dopamine hydrochloride (6.1 molar equivalents) was then added into the reaction and stirred until it was fully dissolved. The reaction was placed in an ice bath, and triethylamine (TEA: 6 molar equivalents) was added dropwise. The reaction was then removed to room temperature and allowed to proceed overnight. Upon completion, the mixture was filtered to remove the triethylamine hydrochloride by-product residue, and the adhesive was precipitated by solvent exchange centrifugation with acidified water (×1; 1:3 v/v). The adhesive was then washed, via solvent exchange centrifugation, with water until neutral (1:4 v/v) and ether (×4; 1:9 v/v). The resulting adhesive was subsequently redissolved in a minimum volume of hot acetone/ethanol (90:10 v/v) and reprecipitated by solvent exchange centrifugation with ether (×4; 1:9 v/v) before being dried for an extended period under vacuum at room temperature to provide Compound 8 as pale yellow hard glassy solid. $^1$H-NMR analysis demonstrated 78% dopamine functionalization.

Scheme 8: Synthesis of polyethylether hexol-derived Compound 8.
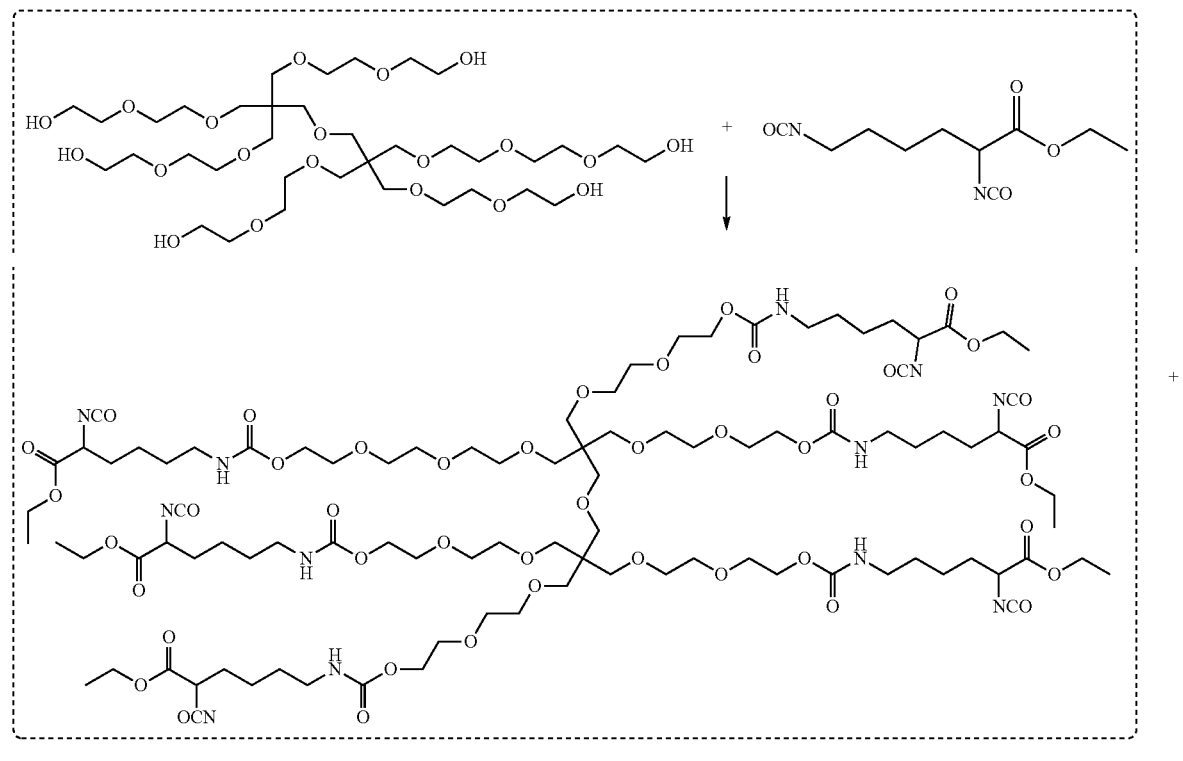
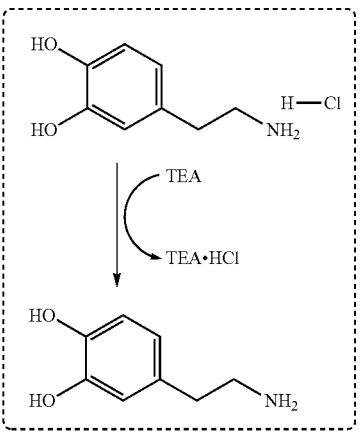

-continued

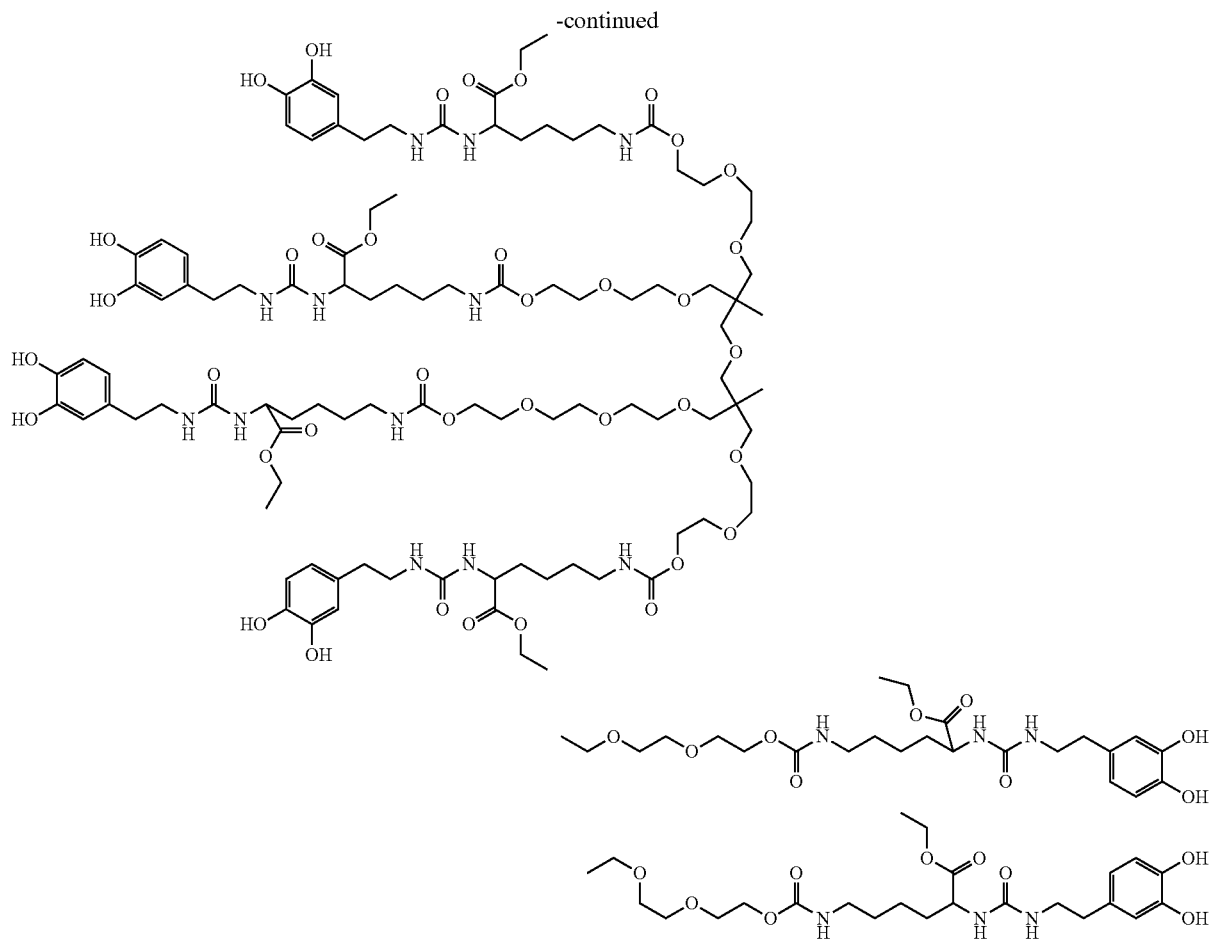

Example 2. Adhesive Blending

Adhesive blends were prepared using a cryogenic milling process. 1-3 g of total mass was added to a steel cannister containing 4 hardened ball bearings. Adhesive blends comprised the adhesives described herein, polymers such as, e.g., PCL (MW=50 kDa, Polysciences, USA), and soluble or insoluble salts such as, e.g., iron(III) phosphate dihydrate (Sigma, USA), iron(III) citrate monohydrate (Sigma USA), sodium chloride (Bioshop, USA), hydroxyapatite (Himed, USA), tetracalcium phosphate (Himed, USA) or sodium carbonate (Bioshop USA). Cryogenic milling of adhesive blends was done on a Retsch Cryomill (Retsch, Del.) with a liquid nitrogen attachment, using three, five-minute milling cycles with auto precool and 5 min cooling between cycles. Milling was done at 30 Hz, and −196° C. Blends were warmed to room temperature inside the cannister before being transferred to a glass scintillation vial. Adhesive blends were dried under vacuum for >2 h at room temperature before being sealed and stored at −20° C. prior to use. Table 1a shows adhesive blends of the disclosure.

TABLE 1a

Adhesive Blends

| | Composition (wt %) | | | |
|---|---|---|---|---|
| Name | Adhesive 1 | Adhesive 2 | Polymer filler | Additive* |
| Blend 1a | Compound 6, 12.5% | Compound 7, 37.5% | Polycaprolactone (PCL$_{50}$; 50 kDa); 50% | — |
| Blend 2a | Compound 4, 12.5% | Compound 7, 37.5% | Polycaprolactone (PCL$_{50}$; 50 kDa); 50% | — |
| Blend 2b | Compound 4, 12.5% | Compound 7, 37.5% | Purasorb PLC7015; 70/30 L-lactide/Caprolactone copolymer (PLC9517), 50% | — |

TABLE 1a-continued

Adhesive Blends

Composition (wt %)

| Name | Adhesive 1 | Adhesive 2 | Polymer filler | Additive* |
|---|---|---|---|---|
| Blend 2c | Compound 4, 12.5% | Compound 7, 37.5% | Poly(L-lactide-co-glycolide); (82:18 lactide:glycolide) (LG824s); 50% | — |
| Blend 2d | Compound 4, 12.5% | Compound 7, 37.5% | Poly(L-lactide) (LG210); 50% | — |
| Blend 2e | Compound 4, 12.5% | Compound 7, 37.5% | Polycaprolactone (PCL$_{14}$; 14 kDa); 50% | — |
| Blend 2f | Compound 4, 12.5% | Compound 7, 37.5% | Compound 3, 50% | — |
| Blend 2g | Compound 4, 12.5% | Compound 7, 37.5% | Pluronic acid (PF127); 50% | — |
| Blend 2h | Compound 4, 12.5% | Compound 7, 37.5% | Hydroxyapatite (HA); 50% | — |
| Blend 2i | Compound 4, 12.5% | Compound 7, 37.5% | Poly(1,4-butylene adipate) (PBA; 12 kDa); 50% | — |
| Blend 3a | Compound 4, 25% | Compound 6, 75% | — | — |
| Blend 3b | Compound 4, 45% | Compound 6, 55% | — | — |
| Blend 3c | Compound 4, 48% | Compound 6, 52% | — | — |
| Blend 3d | Compound 4, 50% | Compound 6, 50% | — | — |
| Blend 3e | Compound 4, 55% | Compound 6, 45% | — | — |
| Blend 3f | Compound 4, 75% | Compound 6, 25% | — | — |
| Blend 4a | Compound 4, 25% | Compound 7, 75% | — | — |
| Blend 4b | Compound 4, 50% | Compound 7, 50% | — | — |
| Blend 4c | Compound 4, 75% | Compound 7, 25% | — | — |
| Blend 5a | Compound 6, 25% | Compound 7, 75% | — | — |
| Blend 5b | Compound 6, 50% | Compound 7, 50% | — | — |
| Blend 5c | Compound 6, 75% | Compound 7, 25% | — | — |
| Blend 6a | Compound 4, 12.5% | Compound 7, 37.5% | Polycaprolactone (PCL$_{50}$; 50 kDa); 50% | NaCl, 1.25% |
| Blend 6b | Compound 4, 12.5% | Compound 7, 37.5% | Polycaprolactone (PCL$_{50}$; 50 kDa); 50% | Na$_2$CO$_3$, 2.5% |
| Blend 6c | Compound 4, 12.5% | Compound 7, 37.5% | Polycaprolactone (PCL$_{50}$; 50 kDa); 50% | NaCl, 2.5% |
| Blend 6d | Compound 4, 12.5% | Compound 7, 37.5% | Polycaprolactone (PCL$_{50}$; 50 kDa); 50% | SiO$_2$, 2.5% |
| Blend 6e | Compound 4, 12.5% | Compound 7, 37.5% | Polycaprolactone (PCL$_{50}$; 50 kDa); 50% | NaCl, 5% |
| Blend 6f | Compound 4, 12.5% | Compound 7, 37.5% | Polycaprolactone (PCL$_{50}$; 50 kDa); 50% | HA, 5% |
| Blend 6g | Compound 4, 12.5% | Compound 7, 37.5% | Polycaprolactone (PCL$_{50}$; 50 kDa); 50% | NaCl, 10% |
| Blend 6h | Compound 4, 12.5% | Compound 7, 37.5% | Polycaprolactone (PCL$_{50}$; 50 kDa); 50% | HA, 20% |
| Blend 6i | Compound 4, 12.5% | Compound 7, 37.5% | Polycaprolactone (PCL$_{50}$; 50 kDa); 50% | HA, 30% |
| Blend 6j | Compound 4, 12.5% | Compound 7, 37.5% | Polycaprolactone (PCL$_{50}$; 50 kDa); 50% | HA, 40% |
| Blend 6k | Compound 4, 12.5% | Compound 7, 37.5% | Polycaprolactone (PCL$_{50}$; 50 kDa); 50% | HA, 60% |
| Blend 6l | Compound 4, 12.5% | Compound 7, 37.5% | Polycaprolactone (PCL$_{50}$; 50 kDa); 50% | HA, 100% |
| Blend 6m | Compound 4, 12.5% | Compound 7, 37.5% | Poly(1,4-butylene adipate) (PBA; 12 kDa); 50% | HA, 60% |
| Blend 6n | Compound 4, 12.5% | Compound 7, 37.5% | Poly(ethylene succinate) (PES; 12 kDa); 50% | HA, 60% |
| Blend 6o | Compound 4, 12.5% | Compound 7, 37.5% | Poly(ethylene adipate) (PEA; 10 kDa); 50% | HA, 60% |
| Blend 7a | Compound 4, 37.5% | Compound 6, 12.5% | Polycaprolactone (PCL$_{50}$; 50 kDa); 50% | — |
| Blend 7b | Compound 4, 25% | Compound 6, 25% | Polycaprolactone (PCL$_{50}$; 50 kDa); 50% | — |
| Blend 7c | Compound 4, 12.5% | Compound 6, 37.5% | Polycaprolactone (PCL$_{50}$; 50 kDa); 50% | — |
| Blend 8a | Compound 6, 37.5% | Compound 7, 12.5% | Polycaprolactone (PCL$_{50}$; 50 kDa); 50% | — |

TABLE 1a-continued

Adhesive Blends

Composition (wt %)

| Name | Adhesive 1 | Adhesive 2 | Polymer filler | Additive* |
|---|---|---|---|---|
| Blend 8c | Compound 6, 12.5% | Compound 7, 37.5% | Polycaprolactone (PCL$_{50}$; 50 kDa); 50% | — |
| Blend 8b | Compound 6, 25% | Compound 7, 25% | Polycaprolactone (PCL$_{50}$; 50 kDa); 50% | — |

*additive weight % is listed as the weight percent of the total organic content; i.e., of Adhesive 1 + Adhesive 2 + Polymer filler.

Example 3. Support Side Preparation

Filaments of polymer blends were created using micro-compounding procedure. Briefly, polymers were dried under vacuum at room temperature overnight prior to use. For films composed of blends of polymers, the polymers were first compounded into filaments using a 10 mL Xplore Twin Screw Micro-compounder at a temperature suitable to melt the polymer (115-220° C. based on the polymers being compounded) for approximately 5 min at 200 rmp. Polymers were extruded into filaments and pelleted.

Pellets were dried under vacuum and then compression molded into thin films on a Carver Automated heated press at 1000 kg. Briefly, platens were heated to a suitable melting temperature. Filaments are cut into ~3 cm lengths to a specific mass, depending on the size of sheet to be pressed. Teflon liners and molds were used to prevent the polymer melt from sticking to the steel platens. Teflon liners were textured in order to impart a texture in the resulting sheet. Teflon molds range in thickness from 0.1-0.5 mm. Molding was done by layering steel sheet, Teflon liner, Teflon mold and polymer material, Teflon liner, and steel sheet. The lamellar molding sandwich was placed on the bottom platen and raised to −1 mm below the top platen. The polymer was melted without any applied force for 10 minutes. After melting, force was increased to −100-300 kg manually. Once the force dropped to −0-100 kg, hydraulic pressure was released to allow any air bubbles to dissipate. Force was then increased in auto mode at 15% speed to 600 kg for 5 minutes. The lamellar mold set up was transferred to a 37° C. and allowed to cool naturally before removing the sheet from the mold. The sheet was trimmed to remove excess material and stored in a desiccator prior to use. Table 1 b shows polymers of the disclosure that make up the support side.

TABLE 1b

Polymeric Supports

| Name | Composition (wt %) | | Compounding temperature (° C.) | Platen temperature (° C.) |
|---|---|---|---|---|
| | Polymer component 1 | Polymer component 2 | | |
| Polymer 1 | Polycaprolactone (PCL; 50 kDa); 100% | — | — | 115 |
| Polymer 2 | Polydioxanone (PDX); 100% | — | — | 130 |
| Polymer Blend 3 | Polydioxanone (PDX); 60% | Polycaprolactone (PCL; 50 kDa); 40% | 115 | 130 |
| Polymer Blend 4 | Polydioxanone (PDX); 80% | Polycaprolactone (PCL; 50 kDa); 20% | 115 | 130 |
| Polymer 5 | Poly(L-lactide-co-glycolide); (82:18 lactide:glycolide) (LG824s), 100% | — | — | 170 |
| Polymer Blend 6 | Poly(L-lactide-co-glycolide); 70/30 L-(82:18 lactide:glycolide) (LG824s), 60% | Purasorb PLC7015; lactide/Caprolactone copolymer (PLC7015), 40% | 185 | 170 |
| Polymer 7 | Purasorb PLC9517; 95/5 L-lactide/Caprolactone copolymer (PLC9517), 100% | — | — | 170 |
| Polymer 8 | Purasorb PLC8516; 85/15 L-lactide/Caprolactone copolymer (PLC8516), 100% | — | — | 170 |
| Polymer Blend 9 | Poly(L-lactide) (LG210) 60% | Purasorb PC17; polycaprolactone (PC17), 40% | 220 | 220 |
| Polymer Blend 10 | Poly(L-lactide-co-glycolide); (82:18 lactide:glycolide) (LG824s), 60% | Polycaprolactone (PCL; 50 kDa); 40% | 185 | 170 |
| Polymer | Purasorb PLC9517; 95/5 L— | Polycaprolactone (PCL; | 185 | 170 |

TABLE 1b-continued

Polymeric Supports

| Name | Composition (wt %) Polymer component 1 | Polymer component 2 | Compounding temperature (° C.) | Platen temperature (° C.) |
|---|---|---|---|---|
| Blend 11 | lactide/Caprolactone copolymer (PLC9517), Purasorb PLC8516; 85/15 L-lactide/Caprolactone copolymer (PLC8516), 40% | 50 kDa); 70% 30% Polycaprolactone (PCL; 50 kDa); 60% | 185 | 170 |
| Polymer Blend 12 | | | | |
| Polymer Blend 13 | Poly(L-lactide-co-glycolide) (82:18 lactide:glycolide) (LG824s), 50% | Purasorb PLC7015; 70/30 L-lactide/Caprolactone copolymer (PLC7015), 50% | 185 | 170 |

Example 4. Texturing Polymer Sheets

In order to create a texture on the adhesion side of the polymer sheets, subtractive, laser etching was used to texture a Teflon liner, as to impart a positive feature in the polymer sheet during compression molding. Textures were created using computer aided design in Autocad. Textures were laser etched into Teflon sheets on a 60 W $CO_2$ laser engraver (Universal Laser Systems, VLS3.5). After etching, textured Teflon sheets were cleaned with isopropanol and compressed air to remove excess material. One polymer sheet was pressed onto the newly etched Teflon liner and removed in order to further clean the textured liner prior to use. Feature dimensions were tuned using more passes or higher power as necessary, but generally measured 100-200 μm in depth. Textured sheets were then used as liners during compression molding of polymer sheets to induce positive features approximately 100-150 μm in height.

Example 5. Device Assembly

Cryomilled adhesive, adhesive blends or adhesive admixtures were sintered onto polymer sheets/films. Briefly, polymer sheets/films were cleaned with isopropyl alcohol and plasma treated under a partial oxygen atmosphere for 10 minutes using a benchtop plasma cleaner (Harrick Plasma, USA). Meanwhile the hot press (Carver, USA) was heated to 75° C. (upper platen) and 70° C. (lower platen). Approximately 0.8 g of adhesive, adhesive blends or adhesive admixtures was placed on to the center of the polymer sheet. The sheet was then placed into a similar laminar mold set up as used for compression molding of the sheet with the adhesion side facing up. The mold thickness was set in order to set the adhesive thickness. The mold was placed on the platen and raised such that the upper platen was <1 mm from the mold. The material was allowed to melt/sinter for 5-10 min under no pressure. After the melt step, 800 kg of force was automatically applied at 15% speed and held for an additional 5 min. The mold was removed and allowed to cool to room temperature before removing the resulting polymer sheet/adhesive composite.

TABLE 1c

Devices Formed from Adhesive Blends and Polymeric Supports

| Bone Tape Name | Adhesive composition | Support side composition |
|---|---|---|
| Device A | Blend 1a | Polymer 4 |
| Device B | Blend 2a | Polymer 4 |
| Device C-1 | Blend 4a | Polymer 3 |
| Device C-2 | Blend 2a | Polymer 3 |
| Device C-3 | Blend 2b | Polymer 3 |
| Device C-4 | Blend 2c | Polymer 3 |
| Device C-5 | Blend 2d | Polymer 3 |
| Device C-6 | Blend 2e | Polymer 3 |
| Device C-7 | Blend 2f | Polymer 3 |
| Device C-8 | Blend 2g | Polymer 3 |
| Device C-9 | Blend 2h | Polymer 3 |
| Device C-10 | Blend 2i | Polymer 3 |
| Device D-1 | Blend 4a | Polymer 3 |
| Device D-2 | Blend 6a | Polymer 3 |
| Device D-3 | Blend 6b | Polymer 3 |
| Device D-4 | Blend 6c | Polymer 3 |
| Device D-5 | Blend 6d | Polymer 3 |
| Device D-6 | Blend 6e | Polymer 3 |
| Device D-7 | Blend 6f | Polymer 3 |
| Device D-8 | Blend 6g | Polymer 3 |
| Device D-9 | Blend 6h | Polymer 3 |
| Device D-10 | Blend 6i | Polymer 3 |
| Device D-11 | Blend 6j | Polymer 3 |
| Device D-12 | Blend 6k | Polymer 3 |
| Device D-13 | Blend 6l | Polymer 3 |
| Device D-14 | Blend 6m | Polymer 3 |
| Device D-15 | Blend 6n | Polymer 3 |
| Device D-16 | Blend 6o | Polymer 3 |
| Device E-1 | Blend 6f | Polymer 1 |
| Device E-2 | Blend 6f | Polymer 2 |
| Device E-3 | Blend 6f | Polymer 3 |
| Device E-4 | Blend 6f | Polymer 4 |
| Device E-5 | Blend 6f | Polymer 5 |
| Device E-6 | Blend 6f | Polymer 6 |
| Device E-7 | Blend 6f | Polymer 7 |
| Device E-8 | Blend 6f | Polymer 8 |

Example 6. Analysis of Thermal Stability and Volatiles Content of Adhesive Compounds The volatiles content of adhesive compounds were obtained from simulated TGA experiments. 100 mg of each adhesive compound was massed in heat resistant glass vials at room temperature. Samples were heated to 160° C. under vacuum condition for 1 hour. After 1 hours, sample were left to cool down under vacuum for another hour. The mass of the samples was recorded after they cooled down. Residual solvent was calculated from the percentage of mass loss obtained at 160° C. 2 samples have been tested for each adhesive.

The results are provided in Table 1d. Table 1d shows the thermal stability/volatile content of the adhesives obtained under simulated thermogravimetric analyses (sTGA), obtained as the material mass loss up to a pre-determined temperature—the boiling point of the highest boiling solvent (160° C. for DMAc, in our case). Thermal stability is important to ensure that the adhesives remain stable during processing, storage, shipment, etc. In brief, 100 mg adhesive samples were heated to 160° C. under vacuum over 1 hour, then allowed to cool under vacuum for another hour before their final masses were determined. Thermal stability/volatiles content was taken as the difference is mass before and after heating.

TABLE 1d

Analysis of Adhesive Compounds

| Adhesive | % Volatiles content (mass loss at 160° C.) |
|---|---|
| Compound 1 | 1.2 ± 0.6 |
| Compound 2 | 1.1 ± 0.2 |
| Compound 3 | 1.1 ± 0.2 |
| Compound 4 | 0.8 ± 0.1 |
| Compound 5 | 1.1 ± 0.2 |
| Compound 6 | 0.0 ± 0.0 |
| Compound 7 | 0.4 ± 0.0 |

Example 8. Analysis of Adhesive Aqueous Solubility and Swelling

The solubility and swelling potential of the adhesive compounds was evaluated. In brief, 0.200 g adhesive samples of were dried under vacuum at 40° C. over 48 h and then weighed to obtain their initial dried mass. 25.0 mL of deionized water was added to each sample, and samples were incubated at room temperature (approximately 21° C.) for 48 h with intermittent mixing. After 48 h, the aqueous phase was decanted, lyophilized, and then vacuum dried overnight at 40° C. in order to determine the mass of material extracted into the water. The ratio of extracted material to the mass of aqueous solution was used to estimate aqueous solubility of each adhesive. The swelling of the residual adhesive, taken as the mass percent of water gained relative to initial adhesive mass, was determined by removing excess water with a kimwipe prior to massing the sample post-incubation. Table 2 shows the solubility and swelling potential of the adhesive compounds.

TABLE 1

Solubility and Swelling Potential of Adhesive Compounds.

| Adhesive | m(Sample) (g) | | Extractable Mass (g) | | Estimated Solubility in diH2O (mg/g) | | Swelling - H2O Mass Gain (%) | |
|---|---|---|---|---|---|---|---|---|
| | Ave | St Dev | Ave | St Dev | Ave | St Dev | Ave | St Dev |
| Compound 1 | 0.2184 | 0.0224 | 0.0040 | 0.0017 | 0.16 | 0.07 | 43.6 | 32.5 |
| Compound 2 | 0.2657 | 0.0084 | 0.0161 | 0.0022 | 0.66 | 0.09 | 98.6 | 8.5 |
| Compound 3 | 0.2068 | 0.0175 | 0.0000 | 0.0002 | 0.00 | 0.01 | 10.3 | 8.1 |
| Compound 4 | 0.2300 | 0.0125 | −0.0006 | 0.0016 | −0.02 | 0.06 | 18.3 | 1.8 |
| Compound 5 | 0.3668 | 0.0672 | 0.0009 | 0.0003 | 0.04 | 0.01 | 6.3 | 2.4 |
| Compound 6 | 0.3357 | 0.0933 | −0.0002 | 0.0003 | −0.01 | 0.01 | 1.9 | 1.9 |
| Compound 7 | 0.2358 | 0.0310 | 0.0003 | 0.0000 | 0.01 | 0.00 | 4.8 | 5.4 |
| Blank | 0.0000 | 0.0003 | 0.0000 | 0.0000 | 0.00 | 0.00 | NA | NA |

All the adhesives tested evidently have low aqueous solubility; the highest average solubility was less than 1 mg/g of water (0.66 mg/g for Compound 2). However, the majority of adhesives tested exhibited solubilities an order of magnitude lower. In two cases (Compounds 4 and 6), the extractable mass was too small to reliably register.

Example 9. Analysis of Thermal Properties of Adhesives

The glass transition temperatures and/or the melting temperatures of the pure adhesives were obtained from Differential Scanning calorimetry (DSC) experiments performed on a DSC7020 Thermal Analysis system (Hitachi High Technologies Canada Inc., ON, Ca) equipped with an electric cooling system. Samples (5-15 mg) were loaded into open 40 μL aluminium DSC pans, and introduced into the DSC sample chamber which was continuously purged with a dry nitrogen flow at 40 mL/min. Each sample was equilibrated at 150° C. for 5 minutes to erase thermal history, cooled to -90° C. at a rate of 20° C./min, held isothermally for 5 min, heated again to 150° C. at a rate of 5° C./min, held isothermally for 5 min, then cooled again to -90° C. at a rate of 5° C./min, held isothermally for 5 min, and finally heated again to 180° C. at a rate of 5° C./min. The melting ($T_M$) and/or glass transition ($T_g$) temperatures were calculated from the thermograms using the Software for NEXTA Standard Analysis, v2.0. The Thermal properties of pure adhesives and adhesive blends are provided in Table 4.

The tackifying temperatures of the pure adhesives were determined as follows. 100 mg adhesive samples were placed in scintillation glass vials and equilibrated to 5 mins in a water bath at room temperature (23° C.). The temperature of the water bath was increased to 75° C. at 1° C./min using the rate-programmable feature of the heating plate. The tackifying temperature was taken at the temperature at which the adhesive changed from a non-flowing rigid/glassy state to a viscous amorphous state that just stringed when prodded with a pipette. Results are presented in Table 3.

TABLE 3

Glass transition temperatures and/or melting temperatures of pure adhesives as obtained from DSC experiments, and tackifying temperatures of the same adhesives.

| Pure Adhesives | $T_g$ (° C.) | Tackifying temperature (° C.) |
| --- | --- | --- |
| Compound 1 | 25.9 ± 1.9 | 40.0 ± 0.6 |
| Compound 2 | 40.8 ± 3.5 | 44.0 ± 1.0 |
| Compound 3 | 52.5 ± 1.5 (Tm) | 49.0 ± 1.0 |
| Compound 4 | 45.7 ± 0.2 | 47.2 ± 0.4 |
| Compound 5 | -10.3 ± 0.3 | 25.0 ± 0.2 |
| Compound 6 | -42.2 ± 5.6 | 29.0 ± 0.5 |
| Compound 7 | 14.7 ± 0.5 | 40.6 ± 0.6 |

Example 10. Analysis of Adhesive Strength

The lap shear strength of the adhesives was obtained by performing standard lap shear tests using an Instron universal testing machine in tensile mode with a 1000 N load cell and a 25 mm/min applied strain rate. Samples (n=6) comprised of adhesive sandwiched between aluminum substrates with a 2×1 cm² contact area and incubated at room temperature overnight prior to testing. The results are provided in Table 4.

TABLE 4

Lap Shear Strength of Adhesives.

| Adhesive | Lap shear strength (kPa) |
| --- | --- |
| Compound 1 | 3091 ± 725 |
| Compound 2 | 3423 ± 906 |
| Compound 3 | 3175 ± 557 |
| Compound 4 | 2359 ± 433 |
| Compound 5 | 1743 ± 297 |
| Compound 6 | 490 ± 192 |
| Compound 7 | 6089 ± 1609 |

Example 11. In Vitro Cell Cytotoxicity

In vitro cell cytotoxicity of Adhesive compounds 4, 6 and 7 as well as the polymer film and the tape device were tested by WST assay. Materials were extracted in growth media (DMEM) at a concentration of 10 mg/mL for compounds and 7 mm²/mL for polymer film and device. Positive and negative controls were treated with 5% DMSO and growth media, respectively. Cells were seeded at the density of 10,000 cells per well. Cell viability was measured after 24 and 72 hours of contact of materials with A10 cells. All materials showed cell viability above the minimum 70% cell viability required for FDA submission except for Compound 4 which had approximately 10% cell viability at both timepoints (FIG. 1). Cytotoxicity of materials was analyzed by direct contact with A10 cells for 24 and 72 hours in comparison to negative and positive controls (DMEM and 5% DMSO, respectively). Cell viability (%) values were determined by WST-1 colorimetric assay. Results are expressed as mean±standard deviation; n=4.

Example 12. Influence of Adhesive Composition on Device Performance

Figure 2:
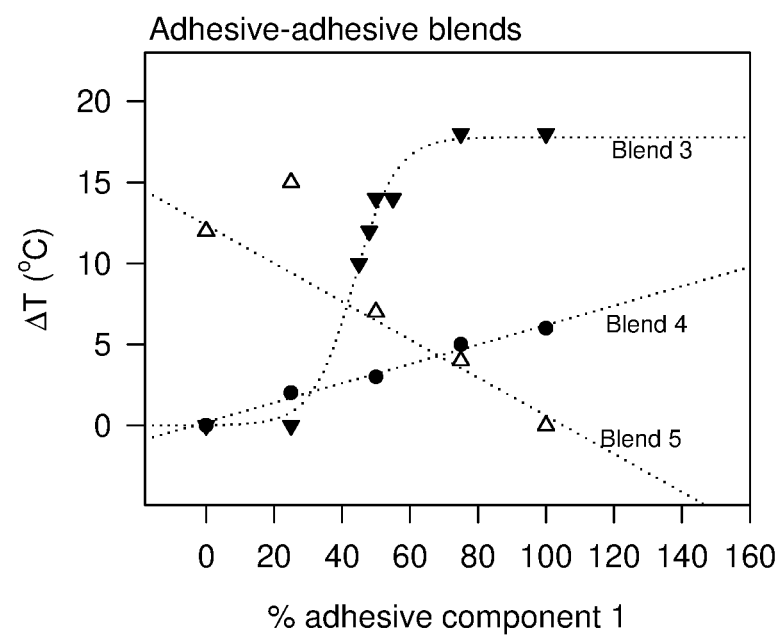
FIG. 2 is a graph showing change in tackifying temperature (normalized to the temperature of the adhesive with the lowest tackifying temperature) of adhesives upon blending with other adhesive compounds.

Adhesive performance could be tuned by varying the composition of the adhesive component. This, however, is not a non-trivial task, as can be seen in FIG. 2 by the non-similar and, therefore, non-obvious dependence of adhesive properties such as tackifying temperature (FIG. 2) on different adhesive components.

Tackifying temperatures and adhesive properties of adhesive-adhesive blend mixtures were evaluated. Blends were prepared by hot mixing select weight ratios of the adhesive components together. 100 mg adhesive samples were placed in scintillation glass vials and equilibrated to 5 mins in a water bath at room temperature (23° C.), following which the temperature of the water bath was increased to 75° C. at 1° C./min using the rate-programmable feature of the heating plate. The tackifying temperature was taken at the temperature at which the adhesive mixture changed from a non-flowing solid to a viscous amorphous state that just stringed when prodded with a pipette. Adhesive properties were determined on adhesive films obtained using an Auto C-PL, H laboratory press (Carver Inc, USA). Approximately 0.1 g of adhesive was placed between Teflon liners and left on the press for 5 min to thermally equilibrate to the 80° C. set temperature. Samples were then compressed at 80° C. for 5 min under a 600 kg load, removed from the press, and given 20 min to cool to room temperature. The Teflon liners were then separated in order to observe the adhesive blends. Adhesive blends were evaluated qualitatively for 1) adhesion to the Teflon and tackiness of the film, 2) stiffness/plasticity/brittleness by bending the Teflon and observing the film for cracking, and 3) cohesion of the film as it was peeled from the Teflon surface.

Table 5 describes the influence of adhesive-adhesive blends, Table 5 shows the influence of the polymer filler within the adhesive blend, and Table 7 shows the influence of particulate adhesives with the adhesive blend.

TABLE 5

Tackifying Temperatures and Adhesive Properties of Adhesive-Adhesive Blend Mixtures.

| Blend | Composition | Mass ratio | Tackifying temperature (° C.) | Adhesion | Brittleness/ Stiffness | Cohesion |
|---|---|---|---|---|---|---|
| 5a | Compound 6: Compound 7 | 25:75 | 44 | adheres, tacky | — | good cohesion, peels |
| 5b | Compound 6: Compound 7 | 50:50 | 36 | adheres, tacky | — | good cohesion, peels |
| 5c | Compound 6: Compound 7 | 75:25 | 33 | adheres, tacky | no cracks, elastic | — |
| 3a | Compound 4: Compound 6 | 25:75 | 29 | adheres, tacky | — | poor cohesion, no peel |
| 3d | Compound 4: Compound 6 | 50:50 | 43 | adheres, tacky | — | poor cohesion, no peel |
| 3f | Compound 4: Compound 6 | 75:25 | 47 | strong adhesion, no tack | brittle - cracks | — |
| 7a | Compound 4: Compound 6: PCL | 37.5:12.5:50 | 49 | poor adhesion (delaminated) | stiff, brittle | peels |
| 7b | Compound 4: Compound 6: PCL | 25:25:50 | 48 | adheres | some stretch, but crazes | peels |
| 7c | Compound 4: Compound 6: PCL | 12.5:37.5:50 | 46 | adheres | tears with little stretch | no peel |
| 8a | Compound 6: Compound 7: PCL | 37.5:12.5:50 | 44 | adheres, no tack | no cracks | poor cohesion, tears w peel |
| 8b | Compound 6: Compound 7: PCL | 12.5:37.5:50 | 47 | adheres, no tack | no cracks, elastic | peeled as whole sheet |
| 8c | Compound 6: Compound 7: PCL | 25:25:50 | 46 | adheres, no tack | no cracks, elastic | peeled as whole sheet |

We evaluated the influence of polymer filler on performance of bone tape Device C, wherein the adhesive component comprises 50% w/w % of adhesive Blend 4a and 50% of the listed polymer filler, and the support side comprises Polymer 3. The bone tape Device was applied using a energy source onto a zygoma covered in citrated horse blood prior to application in order to mimic in vivo application. Tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength. The results are provided in Table 6.

TABLE 6

Influence of Polymer Filler on Performance of Bone Tape Device C.

| Bone Tape | Polymer filler | Ave Score/10 | Tg/Tm of polymer filler | Comments |
|---|---|---|---|---|
| Device C-1 | — | 3 | 43 (Tg) | applies well, poor peel and tension; very brittle |
| Device C-2 | PCL50 | 5 | 60 (Tm); 87 J/g | Applies easily, sticks, mitigates against fluid buildup under bone, poor peel, and good strength. Not brittle |
| Device C-3 | PLC7015 | 1 | 22.8 (Tg) | Does not stay stuck to bone upon removal of applicator |

TABLE 6-continued

Influence of Polymer Filler on Performance of Bone Tape Device C.

| Bone Tape | Polymer filler | Ave Score/10 | Tg/Tm of polymer filler | Comments |
|---|---|---|---|---|
| Device C-4 | LG824s | 0 | −12 (Tg1); 27.5 (Tg2); 56.5 (Tg3), 155 (Tm1); 160 (Tm2) | Does not stick |
| Device C-5 | L210s HA | 0 | 60 (Tg)*; 180 (Tm)* | Does not stick |
| Device C-1Device C-6 | PCL14 | 3 | 60 (Tm)* | applies well, poor peel and tension. brittle |
| Device C-1Device C-7 | Compound 3 | 6.5 | 51 (Tm); 40 J/g | Applies well; good peel and tension. brittle |
| Device C-8 | PF127 (pluronic acid) | 3 | 57 (Tm)* | applies ok; swells and detaches from backing/bone. brittle |
| Device C-9 | HA | 3 | 1100 (Tm)* | applies well, poor peel and tension. brittle |
| Device C-10 | PBA (poly(1,4-butylene adipate)) | 5 | −68 (Tg)*; 54 (Tm)* | Applies well; good peel; poor tension. not brittle |

Table 6 shows that polymer fillers may be used to improve adhesive performance. Without wishing to be bound by theory, this occurs if the polymer filler positively impacts the physical and/or mechanical properties of the adhesive, thereby functioning as a second phase strengthener. For example, polymer fillers with too low (e.g. PLC7015) or too high (e.g. LG824s, L210s HA) softening temperatures restrict the performance of the adhesive layer to below that of the control adhesive (no fillers) itself. Higher molecular weight polymers present improved tensile resistance (e.g. PCL50 versus PCL14, PBA), whilst flexible polymers (e.g. PBA) contribute to improved peel performance. Inorganic fillers, e.g. HA, do not provide the same level of second phase strengthening as the compatible polymer fillers do. Without wishing to be bound by theory, inorganic particulates are typically void fillers, whereas polymer fillers contribute to improved elongation/tensile properties on account of their long chain entanglement interactions.

Polymers which are not miscible with the adhesive compounds (evidenced from distinct adhesive and polymer Tg domains on DSC thermograms), e.g. LG824s and L210s HA, also do not work well, likely because their phase strengthening mechanism is reduced to primarily void filling in the absence of the chain entanglement and the associated intermolecular interactions which are facilitated by phase mixing of the polymer phase with the adhesive compounds. This is corroborated by BT128 which shows that the highest scores are obtained when another adhesive compound with suitable mechanical and/or physical properties is incorporated into the adhesive layer as the polymer filler component.

Polymer fillers which increase the overall hydrophilicity of the adhesive layer, e.g. PF127, will increase the swelling capacity and/or solubility of the adhesive layer, leading to the eventual failure of bone tape via detachment from bone and/or the side support. On the other hand, polymer fillers which decrease the hydrophilicity of the adhesive layer (e.g. PCL) are desirable to mitigate against bone tape failure due to water ingress in vivo.

Example 13. Influence of Particulate Additives on Bone Tape Device Performance

We evaluated the influence of particulate additives on bone tape Device D performance. Varying amounts of the listed particulates were mixed into adhesive formulations comprising 50% wt % of Adhesive Blend 4a and 50% of a polymer filler and assessed for application and adhesion to rabbit zygoma. The bone tape Device was applied using a energy source onto a zygoma covered in citrated horse blood. Wt % reflects amount of inorganic particulate added relative to the adhesive formulation organic mass. Tape performance was assessed qualitatively looking at tape adhesion, ease of application, peel strength, and tensile strength, wherein a score of 0=no adhesion to bone, 5=good application and adhesion to bone and good tensile or good peel strengths; and 10=desirable adhesion, peel resistance and tensile strength. The results are provided in Table 7.

TABLE 7

Influence of Particulate Additives on Bone Tape Device D Performance.

| Bone Tape | Additive | Wt % | Ave Score/10 | Polymer filler |
|---|---|---|---|---|
| Polymer 1 | — | 0 | 0 | $PCL_{50}$ (100%) |
| Device D-1 | none | 0 | 6 | $PCL_{50}$ |
| Device D-2 | NaCl | 1.25 | 4.3 | $PCL_{50}$ |
| Device D-3 | $Na_2CO_3$ | 2.5 | 5 | $PCL_{50}$ |
| Device D-4 | NaCl | 2.5 | 5.5 | $PCL_{50}$ |
| Device D-5 | $SiO_2$ | 2.5 | 5.8 | $PCL_{50}$ |
| Device D-6 | NaCl | 5 | 7.5 | $PCL_{50}$ |
| Device D-7 | HA | 5 | 6.3 | $PCL_{50}$ |
| Device D-8 | NaCl | 10 | 5.5 | $PCL_{50}$ |
| Device D-9 | HA | 20 | 6.25 | $PCL_{50}$ |
| Device D-10 | HA | 30 | 7 | $PCL_{50}$ |
| Device D-11 | HA | 40 | 7.3 | $PCL_{50}$ |
| Device D-12 | HA | 60 | 9.3 | $PCL_{50}$ |
| Device D-13 | HA | 100 | 5.5 | $PCL_{50}$ |
| Device D-14 | HA | 60 | 3.5 | PBA |
| Device D-15 | HA | 60 | 7.5 | PES |
| Device D-16 | HA | 60 | 4 | PEA |

The addition of additives at concentrations less than 2.5 wt % result in no benefit or decreased performance. Additive levels at 2.5 wt % resulted in easier application of tape but no increase in performance was observed. Additive levels at 5-10% resulted in enhanced application and fluid displacement but strength was not noticeably improved. Without wishing to be bound by theory, it is hypothesized that when present in suitable amounts, these additives aid in energy transfer from the backing to the adhesive component, allowing the adhesive component to reach its tackifying temperature without compromising the support side component of bone tape.

Using soluble additives above 10 wt %, however, results in bone tape with compromised integrity upon application as the soluble additive components become dissolved or leached out, leaving behind craters/voids in the bone tape. On the other hand, insoluble additives, e.g. HA, at levels of 20 wt % and above result in improved tensile strength and application as compared to controls. Without wishing to be bound by theory, this may be attributed to the ability of non-soluble additives to function as void filling second phase strengthening agents in addition to aiding with energy transfer from the support to the adhesive component during application. As shown in Table 7 for adhesives containing 60 wt % hydroxyapatite, however, the nature of the polymer filler within the adhesive strongly influences the effectiveness of the additive.

Bone tape with adhesive layers comprising of only the filler polymer PCL, void of adhesive or additives, does not stick to bone.

Example 14. Influence of Support Composition on Bone Tape Device Performance

The influence of support side composition on bone tape Device E. Device E, comprising adhesive Blend 6f on various support side compositions were prepared and assessed for application and adhesion to rabbit zygoma. Application was performed using an ultrasonic heating system. Zygoma was covered in citrated horse blood prior to application in order to mimic in vivo application. Tape performance was assessed qualitatively looking at tape adhesion, ease of application, peel strength, and tensile strength, wherein Y=yes; N=no; and a score of 0=fails, 3=average; and 5=very good performance. The results are provided in Table 8.

PCL with significant crystalline content that undergo rapid melt at temperatures close to or below the tackifying temperature of the adhesive layer. This also applies to polymers which present polymorphic phase transitions and/or which contain multiple polymorphs with phase transitions at or below the tackifying temperature of the adhesive formulation; e.g., PDX presents a final melt temperature at 110° C., but also undergoes several polymorphic transitions inclusive of a melt-mediated recrystallization between room temperature and 50° C.

Polymers which melt/soften at too high temperatures relative to the tackifying temperature of the adhesive formulation (e.g. PLC9517) also present application challenges which translate into compromised device performance. For these systems, the significantly higher temperatures required to soften the support side component in order for it to conform to the shape of the bone surface and thus facilitate the full wetting of the bone surface by the adhesive component actually results in flow out of the adhesive from beneath the bone tape device, leading instead to a compromised device with poor adhesion characteristics. A similar challenge is also observed in polymers with too high elastic moduli ($E_{tensile}$>0.5 GPa; e.g. LG824s, PLC8516), which generally require heating well above their glass transition temperatures in order to improve their flexibility enough so that they could sufficiently contour to the shape of the bone.

Generally, polymers with desired melting profile, tensile strength, and/or elastic modulus could be obtained upon blending of individual polymers, e.g. Polymers 3 and 6 in Table 7 above. We note that support compositions which do not comprise PCL or copolymers containing PCL generally do not adhere well to the adhesive layer. For example, pure PDX backings (Polymer 2) result in delamination of the adhesive layer when the tape is flexed. In a polymer blend, despite being incompatible with nearly all other polymers, PCL contributes to a lower softening temperature, compat-

TABLE 8

Influence of Support Side Composition on Bone Tape Device E.

| Support side | Adhesion to bone | Application Backing melts | Application Adhesive flows | Post application Tension | Post application Peel | Strength [MPa] | Modulus [GPa] | Melting temperature [° C.] | Glass Transition temperature [° C.] |
|---|---|---|---|---|---|---|---|---|---|
| Polymer 1 (PCL) | Y | Y | N | 2 | 4 | 15 ± 1 | 0.2 | 55-60 | — |
| Polymer 2 (PDX) | Y | Y | N | 3 | 3 | 28 ± 1 | 0.4 ± 0.1 | 110 | −16 |
| Polymer Blend 3 (PDX/PCL, 60/40) | Y | N | N | 3 | 3 | 18 ± 4 | 0.6 ± 0.1 | 110, 55 | −16 |
| Polymer 5 (LG824S) | Y | N | Y | 5 | 1 | 63 ± 2 | 2.0 ± 0.2 | | 55 |
| Polymer Blend 6 (LG824S/PLC7015, 60/40) | Y | N | N | 5 | 3 | 25 ± 3 | 0.9 ± 0.1 | | 42 |
| Polymer 7 (PLC9517) | Y | N | Y | 1 | 1 | 60.0* | 2.5* | 164 | 52 |
| Polymer 8 (PLC8516) | Y | Y | Y | 1 | 4 | 53 ± 1 | 1.6 ± 0.2 | | 42 |
| Polymer 9 (LG210 HA) | Y | N | N | 0 | 0 | 55* | 4.3* | 180* | 60* |

Table 8 shows that bone tape performance is strongly dependent upon the properties of the support side component.

Polymers which melt/soften below or at the tackifying temperature of the adhesive formulation (e.g. PCL, PLC7015) are not optimal when used on their own. In these situations, the challenge is the application of the bone tape without introducing defects into the support side component that would compromise the tensile strength of the device post-surgery. This is especially true for polymers such as ibility with the adhesive layer, and strength retention due to its hydrophobicity. Table 9 presents the strength retention profiles of select PCL-containing blends tested over 7 weeks at physiological temperatures (37° C.).

The mechanical properties of polymer blends were measured over the course of seven weeks under physiological conditions to assess their utility for long term use in in vivo settings. Tensile specimens were cut using a laser cutter to approximately 0.5 cm and assessed using a modified ASTM D882-18 standard. The results are provided in Table 9.

TABLE 9

Mechanical properties of polymer blends over 7 weeks under physiological conditions.

| | t = 0 w | | | | t = 3 w | | | | t = 7 w | | | |
|---|---|---|---|---|---|---|---|---|---|---|---|---|
| | Tensile Strength (MPa) | | Elastic Modulus (GPa) | | Tensile Strength (MPa) | | Elastic Modulus (GPa) | | Tensile Strength (MPa) | | Elastic Modulus (GPa) | |
| Material | Ave | StD | Ave | StD | Ave | StD | Ave | StD | Ave | StD | Ave | StD |
| Polymer Blend 10 | 24.27 | 0.49 | 0.63 | 0.03 | 25.22 | 0.47 | 0.73 | 0.01 | 21.94 | 1.67 | 0.83 | 0.05 |
| Polymer Blend 11 | 17.79 | 0.40 | 0.32 | 0.03 | 20.26 | 0.88 | 0.46 | 0.01 | 20.67 | 0.97 | 0.42 | 0.04 |
| Polymer Blend 12 | 18.09 | 0.42 | 0.44 | 0.02 | 20.86 | 0.81 | 0.24 | 0.04 | 20.75 | 2.84 | 0.57 | 0.06 |
| Polymer Blend 13 | 21.52 | 3.08 | 0.59 | 0.10 | 22.08 | 1.25 | 0.49 | 0.10 | 19.66 | 1.98 | 0.56 | 0.14 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

The invention claimed is:

1. A method for reversibly stabilizing bone fragments in a body, the method comprising the steps of:
   (i) forming a first reversible anchor on a first bone fragment by (a) heating an adhesive composition to form a softened adhesive composition and contacting the softened adhesive composition to the first bone fragment, and (b) permitting the softened adhesive composition to cool to form the first anchor affixed to the first bone fragment;
   (ii) forming a second reversible anchor on a second bone fragment by (a) heating an adhesive composition to form a softened adhesive composition and contacting the softened adhesive composition to the second bone fragment, and (b) permitting the softened adhesive composition to cool to form the second anchor affixed to the second bone fragment;
   wherein the adhesive composition has a tackifying temperature of at least 40° C., and
   wherein the first anchor and the second anchor are connected to a support structure for stabilizing the bone fragments; and
   wherein the adhesive composition is not dependent upon in situ curing reactions for adhesion.

2. The method of claim 1, wherein the support structure is a flexible support comprising a biodegradable and biocompatible polymer linking the first anchor to the second anchor.

3. The method of claim 2, wherein the support structure, the first anchor, and the second anchor are formed from a tape comprising (x) a non-adhesive top layer that is the support structure, and (y) a bottom layer that is adhesive when softened to form the first anchor and the second anchor.

4. The method of claim 1, wherein the adhesive composition is not water soluble.

5. The method of claim 1, wherein the adhesive composition comprises a heat transfer agent.

6. The method of claim 5, wherein the heat transfer agent is present in an amount that permits the softened adhesive composition to cool and harden in 120 seconds or less.

7. The method of claim 6, wherein the heat transfer agent is present in an amount that permits the softened adhesive composition to cool and harden in 10 seconds or less.

8. The method of claim 5, wherein the heat transfer agent is present in an amount that permits the adhesive composition to soften within 120 seconds or less of applying energy.

9. The method of claim 8, wherein the heat transfer agent is present in an amount that permits the adhesive composition to soften within 10 seconds or less of applying energy to a non-adhesive top layer.

10. The method of claim 5, wherein the heat transfer agent is selected from the group consisting of sodium chloride, iron(III) phosphate dihydrate, iron(III) citrate monohydrate, hydroxyapatite, tetracalcium phosphate, and sodium carbonate, or a combination thereof.

11. The method of claim 10, wherein the heat transfer agent is hydroxyapatite.

12. The method of claim 5, wherein the adhesive composition comprises about 0.5-60% (w/w) heat transfer agent.

13. The method of claim 12, wherein the adhesive composition comprises about 35-60% (w/w) heat transfer agent.

14. The method of claim 1, wherein the adhesive composition comprises a polymer having the structure of formula (I):

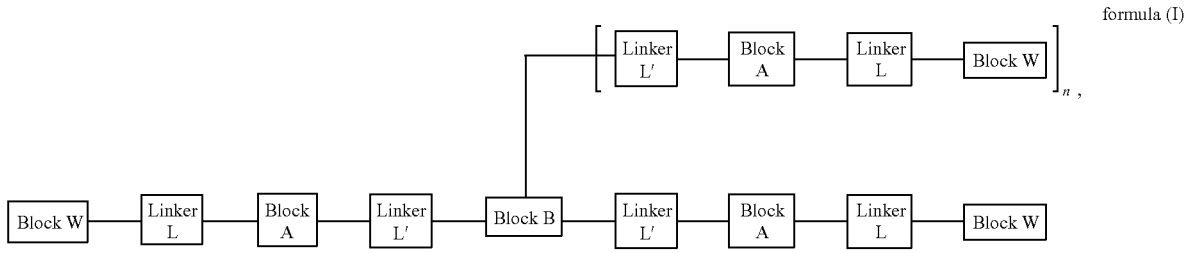

formula (I)

wherein n is an integer from 0 to 4;

Block B comprises an oligomer derived from a polyester, polalkylene glycol, polysilicone, or polycarbonate with a MW≤4,000 g/mol;

Block A comprises an optionally substituted $C_1$-$C_6$ alkylene, wherein Block A is derived from a diisocyanate crosslinker;

Block W comprises an optionally substituted $C_0$-$C_3$ alkyl-benzene-diol or optionally substituted $C_0$-$C_3$ alkyl-benzene-triol;

Linker L' comprises a carbamate; and

Linker L comprises a urea.

15. The method of claim 14, wherein Block B has the structure of formula (II):

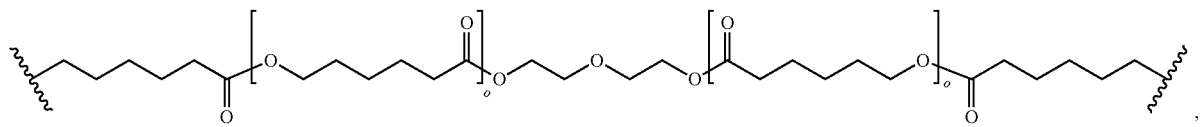

formula (II)

wherein each o is, independently, an integer from 0 to 20.

16. The method of claim 14, wherein Block B has the structure of formula (III):

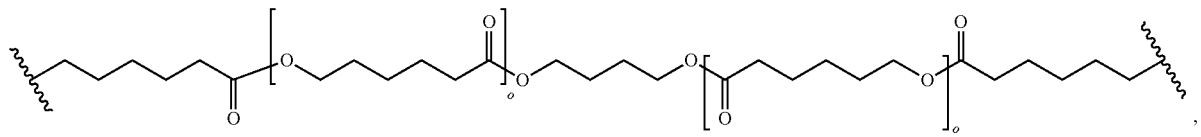

formula (III)

wherein each o is, independently, an integer from 0 to 20.

17. The method of claim 14, wherein Block B has the structure of formula (IV):

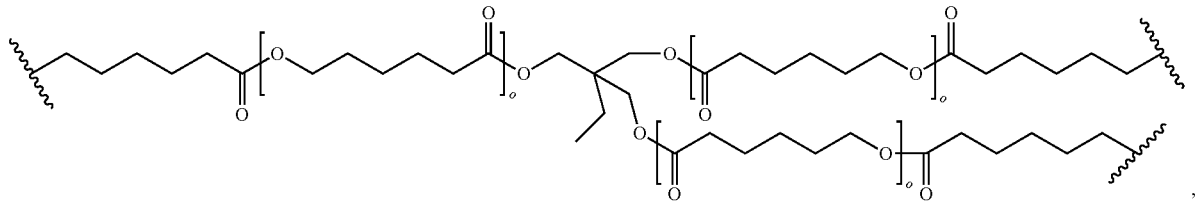

formula (IV)

wherein each o is, independently, an integer from 0 to 20.

18. The method of claim 14, wherein Block B has the structure of formula (V)

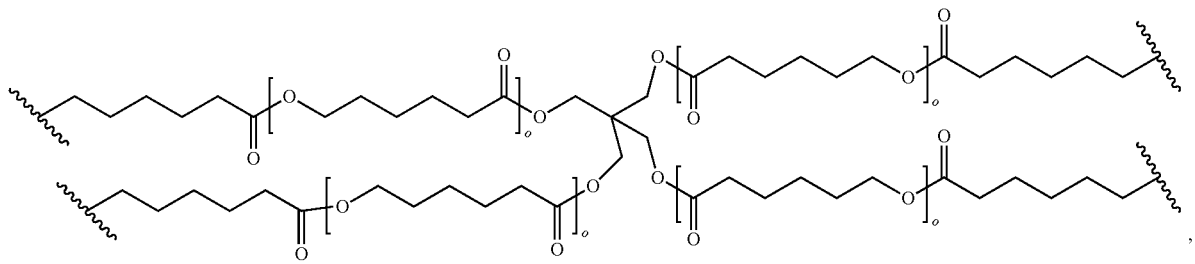

formula (V)

wherein each o is, independently, an integer from 0 to 20.

19. The method of claim 14, wherein Block A has the structure of formula (VII):

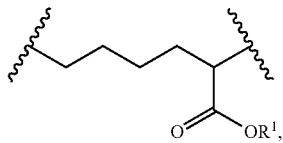

formula (VII)

wherein $R^1$ is $C_1$-$C_3$ alkyl.

20. The method of claim 14, wherein Linker L' has the structure:

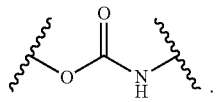

21. The method of claim 14, wherein Linker L has the structure:

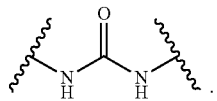

22. The method of claim 14, wherein Block W has the structure:

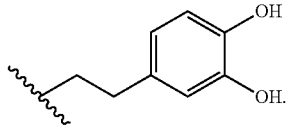 [SMILES: *CCc1ccc(O)c(O)c1]

23. The method of claim 1, wherein the adhesive composition comprises from 30-70% (w/w) of a filler.

24. The method of claim 23, wherein the filler comprises polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof, or a blend thereof.

25. The method of claim 24, wherein the filler comprises polycaprolactone (PCL), polydioxanone (PDX), poly(lactic-co-glycolic acid) (PLGA), or poly-3-hydroxybutyrate (P3HB), or a copolymer thereof, or a blend thereof.

26. The method of claim 23, wherein the filler comprises hydroxyapatite (HA).

27. The method of claim 1, wherein step (i) and step (ii) are repeated to stabilize a plurality of bone fragments in a subject.

28. The method of claim 27, wherein from 2 to 5 or more bone fragments are stabilized in a subject.

29. The method of claim 1, wherein the support structure, the first anchor, and the second anchor are formed from a tape comprising (x) a non-adhesive top layer that is the support structure, and (y) a bottom layer that is adhesive when softened to form the first anchor and the second anchor.

30. The method of claim 29, wherein the non-adhesive polymeric top layer comprises polycaprolactone (PCL), polydioxanone (PDX), poly(lactic-co-glycolic acid) (PLGA), poly-3-hydroxybutyrate (P3HB), poly lactic acid (PLA), polyglycolide (PGA), poly-4-hydroxybutyrate (P4HB), polyethylene carbonate (PEC), polypropylene carbonate (PPC), poly(trimethylene carbonate) (PTMC), polysulfone, polyethylene glycol (PEG), or a copolymer thereof.

* * * * *